United States Patent
Welsh et al.

(10) Patent No.: US 12,053,258 B2
(45) Date of Patent: Aug. 6, 2024

(54) LOCALIZATION SYSTEM AND METHOD USEFUL IN THE ACQUISITION AND ANALYSIS OF CARDIAC INFORMATION

(71) Applicant: Acutus Medical, Inc., Carlsbad, CA (US)

(72) Inventors: Daniel J. Welsh, Encinitas, CA (US); Marcus F. Julian, Vista, CA (US); Graydon E. Beatty, Bloomington, MN (US); Xinwei Shi, San Diego, CA (US); Derrick R. Chou, San Diego, CA (US); Randell L. Werneth, Rancho Santa Fe, CA (US); J. Christopher Flaherty, Auburndale, FL (US); Mark MacGregor, Inver Grove Heights, MN (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 1140 days.

(21) Appl. No.: 16/849,045

(22) Filed: Apr. 15, 2020

(65) Prior Publication Data

US 2020/0352439 A1 Nov. 12, 2020

Related U.S. Application Data

(63) Continuation of application No. 15/569,457, filed as application No. PCT/US2016/032420 on May 13, 2016, now Pat. No. 10,653,318.
(Continued)

(51) Int. Cl.
*A61B 5/06* (2006.01)
*A61B 5/00* (2006.01)
(Continued)

(52) U.S. Cl.
CPC ............ *A61B 5/004* (2013.01); *A61B 5/0035* (2013.01); *A61B 5/0044* (2013.01); *A61B 5/061* (2013.01);
(Continued)

(58) Field of Classification Search
CPC ......... A61B 5/061; A61B 5/287; A61B 5/308; A61B 5/343; A61B 5/6858; A61B 8/0883;
(Continued)

(56) References Cited

U.S. PATENT DOCUMENTS 4,173,228 A 11/1979 Van Steenwyk et al.
4,841,977 A 6/1989 Griffith et al.
(Continued)

FOREIGN PATENT DOCUMENTS

CA 2825736 5/2008
CA 2829626 9/2012
(Continued)

OTHER PUBLICATIONS

International Search Report and Written Opinion dated Aug. 11, 2016 issued in corresponding International Application No. PCT/US2016/032017.
(Continued)

*Primary Examiner* — Lindsey G Wehrheim
(74) *Attorney, Agent, or Firm* — Onello & Mello, LLP

(57) ABSTRACT

Provided are a localization system and method useful in the acquisition and analysis of cardiac information. The localization system and method can be used with systems that perform cardiac mapping, diagnosis and treatment of cardiac abnormalities, as examples, and in the retrieval, processing, and interpretation of such types of information. The localization system and method use high impedance inputs, improved isolation, and relatively high drive currents for
(Continued)

pairs of electrodes used to establish a multi-axis coordinate system. The axes can be rotated and scaled to improve localization.

23 Claims, 7 Drawing Sheets

Related U.S. Application Data

(60) Provisional application No. 62/161,213, filed on May 13, 2015.

(51) Int. Cl.
*A61B 5/283* (2021.01)
*A61B 5/287* (2021.01)
*A61B 5/308* (2021.01)
*A61B 5/343* (2021.01)
*A61B 8/08* (2006.01)
*A61B 8/12* (2006.01)
*A61N 1/37* (2006.01)
*A61B 5/316* (2021.01)
*A61B 8/00* (2006.01)
*A61B 34/20* (2016.01)

(52) U.S. Cl.
CPC .............. *A61B 5/063* (2013.01); *A61B 5/283* (2021.01); *A61B 5/287* (2021.01); *A61B 5/308* (2021.01); *A61B 5/343* (2021.01); *A61B 5/6852* (2013.01); *A61N 1/3702* (2013.01); *A61B 5/316* (2021.01); *A61B 5/6853* (2013.01); *A61B 5/6857* (2013.01); *A61B 5/6858* (2013.01); *A61B 5/6859* (2013.01); *A61B 8/0883* (2013.01); *A61B 8/12* (2013.01); *A61B 8/4416* (2013.01); *A61B 34/20* (2016.02); *A61B 2034/2051* (2016.02); *A61B 2034/2063* (2016.02); *A61B 2034/2065* (2016.02); *A61B 2562/0204* (2013.01); *A61B 2562/0209* (2013.01); *A61B 2576/023* (2013.01)

(58) Field of Classification Search
CPC ......... A61B 8/12; A61B 5/0035; A61B 5/004; A61B 5/0044; A61B 5/063; A61B 5/6852; A61B 5/5863; A61B 5/6857; A61B 5/6859; A61B 8/4416; A61B 34/20; A61B 2034/2063; A61B 2034/2065; A61B 2562/0204; A61B 2562/0209; A61B 2576/023; A61B 5/316; A61N 1/3702; G16H 30/40
See application file for complete search history.

(56) References Cited

U.S. PATENT DOCUMENTS

| | | |
|---|---|---|
| 5,041,973 A | 8/1991 | Lebron et al. |
| 5,156,151 A | 10/1992 | Imran |
| 5,293,868 A | 3/1994 | Nardella |
| 5,482,472 A | 1/1996 | Garoni et al. |
| 5,499,981 A | 3/1996 | Kordis |
| 5,555,883 A | 9/1996 | Avitall |
| 5,595,183 A | 1/1997 | Swanson et al. |
| 5,601,084 A | 2/1997 | Sheehan et al. |
| 5,647,367 A | 7/1997 | Lum et al. |
| 5,662,108 A | 9/1997 | Budd et al. |
| 5,722,402 A | 3/1998 | Swanson et al. |
| 5,722,416 A | 3/1998 | Swanson et al. |
| 5,740,808 A | 4/1998 | Panescu et al. |
| 5,749,833 A | 5/1998 | Hakki et al. |
| 5,759,158 A | 6/1998 | Swanson |
| 5,782,239 A | 7/1998 | Webster, Jr. |
| 5,795,298 A | 8/1998 | Vesely et al. |
| 5,795,299 A | 8/1998 | Eaton et al. |
| 5,820,568 A | 10/1998 | Willis |
| 5,830,144 A | 11/1998 | Vesely |
| 5,846,198 A | 12/1998 | Killmann |
| 5,876,336 A | 3/1999 | Swanson et al. |
| 5,928,228 A | 7/1999 | Kordis et al. |
| 5,944,022 A | 8/1999 | Nardella et al. |
| 5,968,040 A | 10/1999 | Swanson et al. |
| 6,014,590 A | 1/2000 | Whayne et al. |
| 6,024,703 A | 2/2000 | Zanelli et al. |
| 6,066,096 A | 5/2000 | Smith et al. |
| 6,086,532 A | 7/2000 | Panescu et al. |
| 6,107,699 A | 8/2000 | Swanson |
| 6,115,626 A | 9/2000 | Whayne et al. |
| 6,187,032 B1 | 2/2001 | Ohyu et al. |
| 6,188,928 B1 | 2/2001 | Noren et al. |
| 6,216,027 B1 | 4/2001 | Willis et al. |
| 6,216,043 B1 | 4/2001 | Swanson et al. |
| 6,240,307 B1 | 5/2001 | Beatty et al. |
| 6,301,496 B1 | 10/2001 | Reisfeld |
| 6,396,198 B1 | 5/2002 | Okimura et al. |
| 6,400,981 B1 | 6/2002 | Govari |
| 6,490,474 B1 | 12/2002 | Willis et al. |
| 6,514,249 B1 | 2/2003 | Maguire et al. |
| 6,556,695 B1 | 4/2003 | Packer et al. |
| 6,574,492 B1 | 6/2003 | Ben-Haim et al. |
| 6,640,119 B1 | 10/2003 | Budd et al. |
| 6,695,785 B2 | 2/2004 | Brisken et al. |
| 6,716,166 B2 | 4/2004 | Govari |
| 6,728,562 B1 | 4/2004 | Budd et al. |
| 6,772,004 B2 | 8/2004 | Rudy |
| 6,773,402 B2 | 8/2004 | Govari et al. |
| 6,824,515 B2 | 11/2004 | Suorsa et al. |
| 6,826,420 B1 | 11/2004 | Beatty et al. |
| 6,826,421 B1 | 11/2004 | Beatty et al. |
| 6,839,588 B1 | 1/2005 | Rudy |
| 6,895,267 B2 | 5/2005 | Panescu et al. |
| 6,939,309 B1 | 9/2005 | Beatty et al. |
| 6,950,689 B1 | 9/2005 | Willis et al. |
| 6,970,733 B2 | 11/2005 | Willis et al. |
| 6,978,168 B2 | 12/2005 | Beatty et al. |
| 6,990,370 B1 | 1/2006 | Beatty et al. |
| 7,187,964 B2 | 3/2007 | Khoury |
| 7,187,973 B2 | 3/2007 | Hauck |
| 7,258,674 B2 | 8/2007 | Hillstead et al. |
| 7,263,397 B2 | 8/2007 | Hauck et al. |
| 7,285,094 B2 | 10/2007 | Nohara et al. |
| 7,285,119 B2 | 10/2007 | Stewart et al. |
| 7,289,843 B2 | 10/2007 | Beatty et al. |
| 7,291,146 B2 | 11/2007 | Steinke et al. |
| 7,351,914 B2 | 4/2008 | Kaneto et al. |
| 7,479,141 B2 | 1/2009 | Kleen et al. |
| 7,505,810 B2 | 3/2009 | Harlev et al. |
| 7,536,218 B2 | 5/2009 | Govari et al. |
| 7,573,182 B2 | 8/2009 | Savage |
| 7,689,261 B2 | 3/2010 | Mohr et al. |
| 7,766,838 B2 | 8/2010 | Yagi et al. |
| 7,841,986 B2 | 11/2010 | He et al. |
| 7,918,793 B2 | 4/2011 | Altmann et al. |
| 7,953,475 B2 | 5/2011 | Harlev et al. |
| 8,103,327 B2 | 1/2012 | Harlev et al. |
| 8,147,486 B2 | 4/2012 | Honour et al. |
| 8,150,499 B2 | 4/2012 | Gelbart et al. |
| 8,175,680 B2 | 5/2012 | Panescu |
| 8,200,314 B2 | 6/2012 | Bladen et al. |
| 8,208,998 B2 | 6/2012 | Beatty et al. |
| 8,221,411 B2 | 7/2012 | Francischelli et al. |
| 8,233,972 B2 | 7/2012 | Zhang |
| 8,311,613 B2 | 11/2012 | Danehorn |
| 8,320,711 B2 | 11/2012 | Altmann et al. |
| 8,346,339 B2 | 1/2013 | Kordis et al. |
| 8,360,786 B2 | 1/2013 | Duryea |
| 8,364,234 B2 | 1/2013 | Kordis et al. |
| 8,412,307 B2 | 4/2013 | Willis et al. |
| 8,417,313 B2 | 4/2013 | Scharf et al. |
| 8,428,690 B2 | 4/2013 | Li et al. |
| 8,447,377 B2 | 5/2013 | Harlev et al. |

(56) References Cited

U.S. PATENT DOCUMENTS

| | | |
|---|---|---|
| 8,454,596 B2 | 6/2013 | Ma et al. |
| 8,465,433 B2 | 6/2013 | Zwirn |
| 8,478,388 B2 | 7/2013 | Nguyen et al. |
| 8,512,255 B2 | 8/2013 | Scharf et al. |
| 8,571,647 B2 | 10/2013 | Harlev et al. |
| 8,700,119 B2 | 4/2014 | Scharf et al. |
| 8,755,861 B2 | 6/2014 | Harlev et al. |
| 8,825,130 B2 | 9/2014 | Just et al. |
| 8,825,134 B2 | 9/2014 | Danehorn |
| 8,918,158 B2 | 12/2014 | Scharf et al. |
| 8,934,988 B2 | 1/2015 | Persson et al. |
| 8,948,837 B2 | 2/2015 | Harlev et al. |
| 8,968,299 B2 | 3/2015 | Kauphusman et al. |
| 8,979,839 B2 | 3/2015 | De La Rama et al. |
| 8,989,842 B2 | 3/2015 | Li et al. |
| 9,011,423 B2 | 4/2015 | Brewster et al. |
| 9,023,027 B2 | 5/2015 | Bar-Tal et al. |
| 9,026,196 B2 | 5/2015 | Curran et al. |
| 9,031,642 B2 | 5/2015 | Ghosh |
| 9,037,259 B2 | 5/2015 | Mathur |
| 9,044,245 B2 | 6/2015 | Condie et al. |
| 9,113,807 B2 | 8/2015 | Koyrakh et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,220,432 B2 | 12/2015 | Bukhman |
| 9,241,687 B2 | 1/2016 | McGee |
| 9,351,789 B2 | 5/2016 | Novichenok et al. |
| D758,596 S | 6/2016 | Perryman et al. |
| 9,358,398 B2 | 6/2016 | Moffitt et al. |
| 9,380,953 B2 | 7/2016 | Houben et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,498,192 B2 | 11/2016 | Hashimshony et al. |
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| D782,686 S | 3/2017 | Werneth et al. |
| 9,585,588 B2 | 3/2017 | Marecki et al. |
| 9,591,990 B2 | 3/2017 | Chen et al. |
| 9,603,651 B2 | 3/2017 | Ghosh |
| 9,610,024 B2 | 4/2017 | Scharf et al. |
| 9,675,266 B2 | 6/2017 | Afonso et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,730,602 B2 | 8/2017 | Harlev et al. |
| 9,757,044 B2 | 9/2017 | Scharf et al. |
| 9,827,039 B2 | 11/2017 | Dandler et al. |
| 9,901,303 B2 | 2/2018 | Olson |
| 9,913,589 B2 | 3/2018 | Scharf et al. |
| 9,968,268 B2 | 5/2018 | Scharf et al. |
| 10,004,459 B2 | 6/2018 | Werneth et al. |
| 10,028,706 B2 | 7/2018 | Brockway et al. |
| 10,082,395 B2 | 9/2018 | Koyrakh et al. |
| 10,201,311 B2 | 2/2019 | Chou et al. |
| 10,296,707 B2 | 5/2019 | Passerini et al. |
| 10,405,828 B2 | 9/2019 | Deladi et al. |
| 2001/0007070 A1 | 7/2001 | Stewart et al. |
| 2002/0026118 A1 | 2/2002 | Govari |
| 2002/0045810 A1 | 4/2002 | Ben-Haim |
| 2002/0099292 A1 | 7/2002 | Brisken et al. |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0120318 A1 | 6/2003 | Hauck |
| 2003/0153907 A1 | 8/2003 | Suorsa et al. |
| 2003/0158477 A1 | 8/2003 | Panescu |
| 2003/0163046 A1 | 8/2003 | Nohara et al. |
| 2003/0176799 A1 | 9/2003 | Beatty et al. |
| 2003/0231789 A1 | 12/2003 | Willis et al. |
| 2003/0236466 A1 | 12/2003 | Tarjan et al. |
| 2004/0039312 A1 | 2/2004 | Hillstead et al. |
| 2004/0082870 A1 | 4/2004 | Rudy et al. |
| 2004/0082948 A1 | 4/2004 | Stewart et al. |
| 2004/0113498 A1 | 6/2004 | Kroenke |
| 2004/0254437 A1* | 12/2004 | Hauck .................. A61N 1/3702 |
| | | 600/374 |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2006/0244177 A1 | 11/2006 | Kaneto et al. |
| 2007/0016007 A1 | 1/2007 | Govari et al. |
| 2007/0055150 A1 | 3/2007 | Donaldson et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0167722 A1 | 7/2007 | Bladen et al. |
| 2007/0232949 A1 | 10/2007 | Saksena |
| 2008/0009758 A1 | 1/2008 | Voth |
| 2008/0146937 A1 | 6/2008 | Lee et al. |
| 2008/0221438 A1 | 9/2008 | Chen et al. |
| 2008/0287777 A1 | 11/2008 | Li et al. |
| 2008/0319297 A1 | 12/2008 | Danehorn |
| 2009/0024086 A1 | 1/2009 | Zhang et al. |
| 2009/0076483 A1 | 3/2009 | Danehorn |
| 2009/0082691 A1 | 3/2009 | Denison et al. |
| 2009/0131930 A1 | 5/2009 | Gelbart et al. |
| 2009/0143651 A1 | 6/2009 | Kallback et al. |
| 2009/0148012 A1 | 6/2009 | Altmann et al. |
| 2009/0171274 A1 | 7/2009 | Harlev et al. |
| 2009/0264781 A1 | 10/2009 | Scharf et al. |
| 2010/0023004 A1 | 1/2010 | Francischelli et al. |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0256627 A1 | 10/2010 | Ma et al. |
| 2010/0279263 A1 | 11/2010 | Duryea |
| 2010/0286551 A1 | 11/2010 | Harlev et al. |
| 2010/0298690 A1 | 11/2010 | Scharf et al. |
| 2011/0045130 A1 | 2/2011 | Edens et al. |
| 2011/0077526 A1 | 3/2011 | Zwirn |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0144510 A1 | 6/2011 | Ryu et al. |
| 2011/0172658 A1 | 7/2011 | Gelbart et al. |
| 2011/0201951 A1 | 8/2011 | Zhang |
| 2011/0213231 A1 | 9/2011 | Hall et al. |
| 2011/0230775 A1 | 9/2011 | Barley et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0123296 A1 | 5/2012 | Hashimshony et al. |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172702 A1 | 7/2012 | Koyrakh et al. |
| 2012/0172859 A1 | 7/2012 | Condie et al. |
| 2012/0184863 A1 | 7/2012 | Harlev et al. |
| 2012/0265054 A1* | 10/2012 | Olson ................... A61B 34/20 |
| | | 600/424 |
| 2012/0271138 A1 | 10/2012 | Kordis et al. |
| 2012/0271139 A1 | 10/2012 | Kordis et al. |
| 2012/0277574 A1 | 11/2012 | Panescu |

(56) References Cited

U.S. PATENT DOCUMENTS

| | | |
|---|---|---|
| 2012/0302912 A1 | 11/2012 | Moffitt et al. |
| 2012/0310064 A1 | 12/2012 | McGee |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |
| 2013/0165916 A1 | 6/2013 | Mathur |
| 2013/0172715 A1 | 7/2013 | Just et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0241929 A1 | 9/2013 | Massarwa et al. |
| 2013/0245433 A1 | 9/2013 | Deladi et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0095105 A1 | 4/2014 | Koyrakh et al. |
| 2014/0121470 A1 | 5/2014 | Scharf et al. |
| 2014/0148677 A1 | 5/2014 | Liempde et al. |
| 2014/0180150 A1 | 6/2014 | Scharf et al. |
| 2014/0221803 A1 | 8/2014 | Bar-Tal et al. |
| 2014/0235988 A1 | 8/2014 | Ghosh |
| 2014/0249505 A1 | 9/2014 | Bukhman |
| 2014/0257069 A1 | 9/2014 | Eliason et al. |
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0358143 A1 | 12/2014 | Novichenok et al. |
| 2015/0038862 A1 | 2/2015 | Gijsbers et al. |
| 2015/0196217 A1 | 7/2015 | Harlev et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0223863 A1 | 8/2015 | Ghosh |
| 2015/0257732 A1 | 9/2015 | Ryan |
| 2015/0257825 A1 | 9/2015 | Kelly et al. |
| 2015/0294082 A1 | 10/2015 | Passerini et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0192902 A1 | 7/2016 | Werneth et al. |
| 2016/0256112 A1 | 9/2016 | Brockway et al. |
| 2017/0035486 A1 | 2/2017 | Lopes et al. |
| 2017/0065204 A1 | 3/2017 | Ludwin et al. |
| 2017/0100049 A1 | 4/2017 | Scharf et al. |
| 2017/0202469 A1 | 7/2017 | Scharf et al. |
| 2017/0258347 A1 | 9/2017 | Scharf et al. |
| 2017/0311833 A1 | 11/2017 | Afonso et al. |
| 2017/0319180 A1 | 11/2017 | Henneken et al. |
| 2018/0055374 A1 | 3/2018 | Scharf et al. |
| 2018/0146948 A1 | 5/2018 | Chou et al. |
| 2019/0159729 A1 | 5/2019 | Chou et al. |
| 2020/0138317 A1 | 5/2020 | Scharf et al. |
| 2020/0187801 A1 | 6/2020 | Scharf et al. |

FOREIGN PATENT DOCUMENTS

| | | |
|---|---|---|
| CN | 1856123 | 11/2006 |
| CN | 101048100 | 10/2007 |
| CN | 201223445 | 4/2009 |
| CN | 201275144 | 7/2009 |
| CN | 102770085 | 11/2012 |
| CN | 104462650 | 3/2015 |
| EP | 1166714 | 1/2002 |
| EP | 1415608 | 10/2004 |
| EP | 1760661 | 3/2007 |
| EP | 1779787 | 5/2007 |
| EP | 2051625 | 4/2009 |
| EP | 2252203 | 11/2010 |
| EP | 2683293 | 1/2014 |
| EP | 2953550 | 8/2016 |
| JP | 08501477 | 2/1996 |
| JP | 08504333 | 5/1996 |
| JP | 08164140 | 6/1996 |
| JP | 10137207 | 5/1998 |
| JP | 11504541 | 4/1999 |
| JP | 2000510030 | 8/2000 |
| JP | 2000510250 | 8/2000 |
| JP | 2000358299 | 12/2000 |
| JP | 2001070269 | 3/2001 |
| JP | 2001522288 | 11/2001 |
| JP | 2002051998 | 2/2002 |
| JP | 2002113004 | 4/2002 |
| JP | 2002522106 | 7/2002 |
| JP | 2003509145 | 3/2003 |
| JP | 2003511098 | 3/2003 |
| JP | 2004350702 | 12/2004 |
| JP | 2005536313 | 12/2005 |
| JP | 2006511296 | 4/2006 |
| JP | 2006525072 | 11/2006 |
| JP | 2008149132 | 7/2008 |
| JP | 2009135109 | 6/2009 |
| JP | 2009136679 | 6/2009 |
| JP | 2011504363 | 2/2011 |
| JP | 2011507656 | 3/2011 |
| JP | 2012509701 | 4/2012 |
| JP | 2013188476 | 9/2013 |
| JP | 2014506171 | 3/2014 |
| JP | 2014514031 | 6/2014 |
| JP | 2014516723 | 7/2014 |
| JP | 2016511026 | 4/2016 |
| JP | 2017514553 | 6/2017 |
| WO | 9406349 | 3/1994 |
| WO | 9905971 | 2/1999 |
| WO | 0007501 | 2/2000 |
| WO | 0040166 | 7/2000 |
| WO | 0245608 | 6/2002 |
| WO | 03026722 | 4/2003 |
| WO | 2004026134 | 4/2004 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012068471 | 5/2012 |
| WO | 2012092016 | 7/2012 |
| WO | 2012100184 | 7/2012 |
| WO | 2012100185 | 7/2012 |
| WO | 2012110942 | 8/2012 |
| WO | 2012122517 | 9/2012 |
| WO | 2014124231 | 2/2013 |
| WO | 2013101257 | 7/2013 |
| WO | 2013123549 | 8/2013 |
| WO | 2014036439 | 3/2014 |
| WO | 20014059308 | 4/2014 |
| WO | 2014130169 | 8/2014 |
| WO | 2014137897 | 9/2014 |
| WO | 2015038607 | 3/2015 |
| WO | 2015148470 | 10/2015 |
| WO | 2016183179 | 11/2016 |
| WO | 2016183285 | 11/2016 |
| WO | 2016183468 | 11/2016 |
| WO | 2017192769 | 11/2017 |
| WO | 2017192775 | 11/2017 |
| WO | 2019144103 | 7/2019 |

(56) References Cited

FOREIGN PATENT DOCUMENTS

| WO | 2019217430 | 11/2019 |
|---|---|---|
| WO | 2020097438 | 5/2020 |

OTHER PUBLICATIONS

International Search Report and Written Opinion dated Aug. 18, 2016 issued in corresponding International Application No. PCT/US16/32420.
International Search Report and Written Opinion dated Aug. 4, 2017 issued in corresponding International Application No. PCT/US17/30915.
International Search Report and Written Opinion dated Aug. 8, 2016 issued in corresponding European Application No. PCT/US2016/031823.
International Search Report and Written Opinion dated Dec. 12, 2017 issued in corresponding International Application No. PCT/US2017/056064.
International Search Report and Written Opinion dated Jan. 14, 2020 issued in International Application No. PCT/US2019/060433.
International Search Report and Written Opinion dated Jul. 23, 2019 issued in corresponding International Application No. PCT/US2019/031131.
International Search Report and Written Opinion dated Jun. 26, 2015 issued in International Application No. PCT/US2015/022187.
International Search Report and Written Opinion dated Jun. 5, 2014 issued in corresponding International Application No. PCT/US2013/057579.
International Search Report and Written Opinion dated Mar. 10, 2015 issued in corresponding International Application No. PCT/US14/54942.
International Search Report and Written Opinion dated Mar. 5, 2013 issued in corresponding International Application No. PCT/US2012/028593.
International Search Report and Written Opinion dated May 20, 2014 issued in corresponding International Application No. PCT/US14/15261.
International Search Report and Written Opinion dated Sep. 25, 2017, issued in corresponding Application No. PCT/US17/30922.
International Search Report dated Oct. 7, 2009 issued in corresponding International Application No. PCT/IB2009/000071.
International Search Report issued Apr. 21, 2008 in related International Application No. PCT/CH2007/000380.
Invitation to Pay Additional Fees issued on Jan. 8, 2014 in corresponding International Application No. PCT/US2013/057579.
Japanese Notice of Allowance dated Feb. 27, 2018 issued in corresponding Japanese Application No. 2015-530101, with English language translation.
Japanese Notice of Allowance dated Jul. 11, 2017 issued in corresponding Japanese Application No. 2013-557-926, with English language summary.
Japanese Notice of Allowance dated Jun. 11, 2019 issued in corresponding Japanese Application No. 2018-024907, with English translation.
Japanese Notice of Allowance dated Mar. 5, 2019 issued in corresponding Japanese Application No. 2018061040, with English translation.
Japanese Notice of Allowance dated Sep. 18, 2018 issued in corresponding Japanese Application No. 2015-557091, with English language translation.
Japanese Office Action dated Aug. 28, 2018 issued in corresponding Japanese Application No. 2016-542062, with machine translation to English.
Japanese Office Action dated Dec. 11, 2018 issued in corresponding Japanese Application No. 2018-024907, with machine translation to English.
Japanese Office Action dated Feb. 16, 2016 issued in corresponding Japanese Application No. 2013-557-926, with English language summary.
Japanese Office Action dated Feb. 19, 2019 issued in corresponding Japanese Application No. 2016-558799, with machine translation to English.
Japanese Office Action dated Jan. 31, 2017 issued in corresponding Japanese Application No. 2013-557-926, with English language summary.
Japanese Office Action dated Jul. 23, 2019 issued in corresponding Japanese Application No. 2016-542062, with machine translation to English.
Japanese Office Action dated Jun. 27, 2017 issued in corresponding Japanese Application No. 2015-530101, with English language translation.
Japanese Office Action dated Mar. 10, 2020 issued in corresponding Japanese Application No. 2017-559320, with machine translation to English.
Japanese Office Action dated Mar. 17, 2020 issued in corresponding Japanese Application No. 2019-071004, with machine translation to English.
Japanese Office Action dated Oct. 10, 2017 issued in corresponding Japanese Application No. 2015-557091, with machine translation to English.
Japanese Office Action dated Oct. 15, 2019 issued in corresponding Japanese Application No. 2018-195960, with machine translation to English.
Japanese Office Action dated Sep. 26, 2017 issued in corresponding Japanese Application No. 2017-155346, with English translation.
Summons to Attend Oral Proceedings dated Dec. 20, 2019 issued in corresponding European Application No. 13763151.1.
Della Bella et al. "Non-contact mapping to guide catheter ablation of untolerated ventrical tachycardia" European Heart Journal, May 2002, 23(9)742-752.
Gupta et al. "Point of View Cardiac Mapping: Utility or Futility?", Indian Pacing and Electrophysiology Journal, vol. 2, No. 1, 2002, pp. 20-32.
He et al. "An equivalent body surface charge model representing three-dimensional bioelectrical activity" IEEE Transactions on Biomedical Engineering, 42.7 (Jul. 7, 1995) pp. 637-646.
Jackson, JD, "Surface Distributions of Charges and Dipoles and Discontinuities in the Electric Field and Potential", Classical Electrodynamics, 3rd edition, Dec. 1998, pp. 31-34.
Leif et al., "Geometric modeling based on polygonal meshes". Eurographics 2000 Tutorial, Aug. 21, 2000.
Partial European Search Report dated Apr. 29, 2014 issued in corresponding European U.S. Appl. No. 13/176,658.
Pullan et al. "The inverse problem of electrocardiology" Northeastern University Electrical and Computer Engineering, Feb. 23, 2007.
Stevenson et al. "Recording Techniques for Clinical Electrophysiology", Journal of Cardiovascular Electrophysiology, vol. 16, No. 9, Sep. 2005, pp. 1017-1022.
Van Oosterom A: "Solidifying the solid angle." 2002 Journal of Electrocardiology 2002 vol. 35 Suppl pp. 181-192 ISSN: 0022-0736.
Wolfgang Nolting: Elektrodynamik—Grundkurs Theoretische Physik 3, Springer Spectrum, p. 89-91.
International Search Report and Written Opinion dated Jul. 21, 2020 issued in corresponding International Application No. PCT/US2020/028779.
Japanese Office Action dated Jul. 28, 2020 issued in corresponding Japanese Application No. 2018-195960, with machine translation to English.
Japanese Office Notice of Allowance dated Sep. 1, 2020 issued in corresponding Japanese Application No. 2017-559320, with English summary.
Summons to Attend Oral Proceedings dated May 9, 2023 issued in corresponding European Application No. 16793622.8.
Canadian Office Action dated May 20, 2020 issued in corresponding Canadian Application No. 2881457.
European Office Action dated Jun. 15, 2020 issued in corresponding European Application No. 15768711.2.
Japanese Office Action dated Jan. 7, 2020 issued in corresponding Japanese Application No. 2016-558799, with machine translation to English.

(56) References Cited

OTHER PUBLICATIONS

Anatomy Warehouse, "Axis Heart Model", 2014, pp. 1-3, at http://www.anatomywarehouse.com/axis-scientific-2-part-deluxe-life-size-human-heart-a-104269. (Year: 2014).
Christoph Scharf et al. Declaration under 37 C.F.R. 1.132, Nov. 15, 2012.
Australian Examination Report dated Feb. 8, 2019 issued in corresponding Australian Application No. 2018250516.
Australian Examination Report dated Jun. 28, 2018 issued in corresponding Australian Patent Application No. 2014318872.
Australian Office Action dated Dec. 22, 2019 issued in corresponding Australian Application No. 2018278959.
Australian Office Action dated Feb. 26, 2018 issued in Australian Application No. 2017201560.
Australian Office Action dated Jan. 15, 2020 issued in corresponding Australian Application No. 2016262547.
Australian Office Action dated Jan. 26, 2019 issued in corresponding Australian Application No. 2018211348.
Australian Office Action dated Jul. 6, 2017 issued in corresponding Australian Application No. 2014214756.
Australian Office Action dated Jun. 14, 2018 issued in Australian Application No. 2014214756.
Australian Office Action dated Jun. 27, 2017 issued in corresponding Australian Application No. 2013308531.
Australian Office Action dated Mar. 16, 2020 issued in corresponding Australian Application No. 2016260522.
Australian Office Action dated Mar. 17, 2018 issued in corresponding Australian Application No. 2013308531.
Australian Office Action dated May 30, 2016 issued in related Australian Application No. 2012225250.
Australian Office Action dated Sep. 21, 2016 issued in corresponding Australian Application No. 2012225250.
Canadian Office Action dated Apr. 26, 2017 issued in corresponding Canadian Application No. 2932956.
Canadian Office Action dated Apr. 27, 2016 issued in corresponding Canadian Application No. 2747859.
Canadian Office Action dated Dec. 22 2015 issued in corresponding Canadian Application No. 2656898.
Canadian Office Action dated Jan. 22, 2018 issued in corresponding Canadian Application No. 2932956.
Canadian Office Action dated Jul. 12, 2019 issued in corresponding Canadian Application No. 2881457.
Canadian Office Action dated Mar. 30, 2017 issued in corresponding Canadian Application No. 2747859.
Canadian Office Action dated Nov. 27, 2017 issued in corresponding Canadian Application No. 2829626.
Canadian Office Action dated Nov. 7, 2018 issued in corresponding Canadian Application No. 2932956.
Canadian Office Action dated Oct. 29, 2018 issued in corresponding Canadian Application No. 2829626.
Canadian Office Action dated Oct. 4, 2013 issued in corresponding Canadian Application No. 2659898.
Chinese Office Action dated Apr. 17, 2017 issued in corresponding Chinese Application No. 201480018328.4.
Chinese Office Action dated Apr. 8, 2020 issued in corresponding Chinese Application No. 201810153436.2.
Decision dated Jan. 16, 2018 issued for European Patent Application No. 09702094.5.
Decision dated Jan. 18, 2018 issued for European Patent Application No. 13176658.6.
European Office Action dated Apr. 23, 2018 issued in corresponding European Application No. 07785075.8.
European Office Action dated Apr. 28, 2014 issued in corresponding European Application No. 09702094.5.
European Office Action dated Feb. 29, 2016 issued in corresponding European Application No. 07785075.8.
European Office Action dated Feb. 6, 2019 issued in corresponding European Application No. 14843283.4.
European Office Action dated Jan. 28, 2019 issued in corresponding European Application No. 14748567.6.
European Office Action dated Jan. 31, 2018 issued in corresponding European Application No. 13763151.1.
European Office Action dated Mar. 21, 2017 issued in corresponding European Application No. 07785075.8.
European Office Action dated Mar. 9, 2016 issued in corresponding European Application No. 09702094.5.
European Office Action dated Mar. 9, 2016 issued in corresponding European Application No. 13176658.6.
European Office Action dated Nov. 7, 2017 issued in corresponding European Application No. 15768711.
Extended European Search Report dated Dec. 5, 2018 issued in corresponding European Application No. 16793622.8.
Extended European Search Report dated Jul. 8, 2016 issued in corresponding European Application No. 14748567.6.
Extended European Search Report dated Mar. 14, 2017 issued in corresponding European Application No. 14843283.4.
Extended European Search Report dated Nov. 26, 2019 issued in corresponding European Application No. 19184148.5.
Extended European Search Report dated Oct. 18, 2017 issued in European Application No. 15768711.
Extended European Search Report dated Oct. 4, 2018 issued in corresponding European Application No. 16793503.0.
Extended European Search Report dated Sep. 29, 2014 issued in corresponding European Application No. 13176658.
International Search Report and Written Opinion dated Apr. 8, 2019, issued in corresponding International Application No. PCT/US19/14498.
Japanese Office Action dated Nov. 2, 2021 issued in corresponding Japanese Application No. 2020-192741, with English translation.
Communication Under Rule 71(3) EPC dated Nov. 15, 2021 issued in corresponding European Application No. 15768711.2.
Extended European Search Report dated Dec. 13, 2021 issued in corresponding European Application No. 19800090.3.
Extended European Search Report dated Aug. 10, 2021 issued in corresponding European Application No. 19741310.7.
Flavia et al. "Wave Similarity Mapping Shows the Spatiotemporal Distribution of Fibrillatory Wave Complexity in the Human Right Atrium During Paroxysmal and Chronic Atrial Fibrillation", Journal of Cardiovascular Electrophysiology, vol. 16, No. 10 (Oct. 2005) pp. 1071-1076.
Japanese Notice of Allowance dated Jul. 7, 2020 issued in corresponding Japanese Application No. 2016558799, with English translation of allowed claims.
Japanese Office Action dated Jun. 30, 2020 issued in corresponding Japanese Application No. 2017559317, with machine translation to English.
Extended European Search Report dated Jul. 23, 2021 issued in corresponding European Application No. 21150862.7.
International Search Report and Written Opinion dated Sep. 14, 2020 issued in corresponding International Application No. PCT/US2020/036110.
Chinese Office Action dated Sep. 8, 2021 issued in corresponding Chinese Application No. 201680040709.1.
Japanese Office Action dated Jun. 29, 2021 issued in corresponding Japanese Application No. 2020-081074, with machine translation to English.

* cited by examiner

LOCALIZATION SYSTEM AND METHOD USEFUL IN THE ACQUISITION AND ANALYSIS OF CARDIAC INFORMATION

RELATED APPLICATIONS

The present application is a continuation application of U.S. patent application Ser. No. 15/569,457, filed Oct. 26, 2017, which is a 371 national stage application of Patent Cooperation Treaty Application No. PCT/US2016/032420 filed May 13, 2016, entitled "Localization System and Method Useful in the Acquisition and Analysis of Cardiac Information", which in turn claims priority under 35 USC 119(e) to U.S. Provisional Patent Application Ser. No. 62/161,213, entitled "Localization System and Method Useful in the Acquisition and Analysis of Cardiac Information", filed May 13, 2015, which is incorporated herein by reference in its entirety.

The present application, while not claiming priority to, may be related to U.S. patent application Ser. No. 14/865,435, entitled "Method and Device for Determining and Presenting Surface Charge and Dipole Densities on Cardiac Walls", filed Sep. 25, 2015, which is a continuation of U.S. Pat. No. 9,167,982 (hereinafter the '982 patent), entitled "Method and Device for Determining and Presenting Surface Charge and Dipole Densities on Cardiac Walls", issued Oct. 27, 2015, which is a continuation of U.S. Pat. No. 8,918,158 (hereinafter the '158 patent), entitled "Method and Device for Determining and Presenting Surface Charge and Dipole Densities on Cardiac Walls", issued Dec. 23, 2014, which is a continuation of U.S. Pat. No. 8,700,119 (hereinafter the '119 patent), entitled "Method and Device for Determining and Presenting Surface Charge and Dipole Densities on Cardiac Walls", issued Apr. 15, 2014, which is a continuation of U.S. Pat. No. 8,417,313 (hereinafter the '313 patent), entitled "Method and Device for Determining and Presenting Surface Charge and Dipole Densities on Cardiac Walls", issued Apr. 9, 2013, which was a 35 USC 371 national stage filing of Patent Cooperation Treaty Application No. CH2007/000380, entitled "Method and Device for Determining and Presenting Surface Charge and Dipole Densities on Cardiac Walls", filed Aug. 3, 2007, published as WO 2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 14/886,449, entitled "Device and Method For the Geometric Determination of Electrical Dipole Densities on the Cardiac Wall", filed Oct. 19, 2015, which is a continuation of U.S. Pat. No. 9,192,318 (hereinafter the '318 patent), entitled "Device and Method For the Geometric Determination of Electrical Dipole Densities on the Cardiac Wall", issued Nov. 24, 2015, which is a continuation of U.S. Pat. No. 8,512,255, entitled "Device and Method for the Geometric Determination of Electrical Dipole Densities on the Cardiac Wall", issued Aug. 20, 2013, published as US2010/0298690 (hereinafter the '690 publication), which was a 35 USC 371 national stage application of Patent Cooperation Treaty Application No. PCT/1609/00071 filed Jan. 16, 2009, entitled "A Device and Method for the Geometric Determination of Electrical Dipole Densities on the Cardiac Wall", published as WO2009/090547, which claimed priority to Swiss Patent Application 00068/08 filed Jan. 17, 2008, each of which is hereby incorporated by reference.

The present application, while not claiming priority to, may be related to U.S. application Ser. No. 14/003,671, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517 (hereinafter the '517 publication), which claimed priority to U.S. Patent Provisional Application Ser. No. 61/451,357, each of which is hereby incorporated by reference.

The present application, while not claiming priority to, may be related to U.S. Design application Ser. No. 29/475,273, entitled "Catheter System and Methods of Medical Uses of Same, Including Diagnostic and Treatment Uses for the Heart", filed Dec. 2, 2013, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, which claims priority to U.S. Patent Provisional Application Ser. No. 61/695,535, entitled "System and Method for Diagnosing and Treating Heart Tissue", filed Aug. 31, 2012, which is hereby incorporated by reference.

The present application, while not claiming priority to, may be related to U.S. application Ser. No. 14/762,944, entitled "Expandable Catheter Assembly with Flexible Printed Circuit Board (PCB) Electrical Pathways", filed Jul. 23, 2015, which is a 35 USC 371 national stage filing of Patent Cooperation Treaty Application No. PCT/US2014/15261, entitled "Expandable Catheter Assembly with Flexible Printed Circuit Board (PCB) Electrical Pathways", filed Feb. 7, 2014, published as WO2014/124231, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, which is hereby incorporated by reference.

The present application, while not claiming priority to, may be related to Patent Cooperation Treaty Application No. PCT/US2015/11312, entitled "Gas-Elimination Patient Access Device", filed Jan. 14, 2015, which claims priority to U.S. Patent Provisional Application Ser. No. 61/928,704, entitled "Gas-Elimination Patient Access Device", filed Jan. 17, 2014, which is hereby incorporated by reference.

The present application, while not claiming priority to, may be related to Patent Cooperation Treaty Application No. PCT/US2015/22187, entitled "Cardiac Analysis User Interface System and Method", filed Mar. 24, 2015, which claims priority to U.S. Patent Provisional Application Ser. No. 61/970,027, entitled "Cardiac Analysis User Interface System and Method", filed Mar. 28, 2014, which is hereby incorporated by reference.

The present application, while not claiming priority to, may be related to U.S. application Ser. No. 14/916,056, entitled "Devices and Methods for Determination of Electrical Dipole Densities on a Cardiac Surface", filed Mar. 2, 2016, which is a 35 USC 371 national stage filing of Patent Cooperation Treaty Application No. PCT/US2014/54942, entitled "Devices and Methods for Determination of Electrical Dipole Densities on a Cardiac Surface", filed Sep. 10, 2014, published as WO2015/038607, which claims priority to U.S. Patent Provisional Application Ser. No. 61/877,617, entitled "Devices and Methods for Determination of Electrical Dipole Densities on a Cardiac Surface", filed Sep. 13, 2013, which is hereby incorporated by reference.

FIELD

The present invention is generally related to systems and methods that may be useful for the diagnosis and treatment of cardiac arrhythmias or other abnormalities, in particular, the present invention is related to systems, devices, and methods useful in performing localization of such arrhythmias or other abnormalities.

BACKGROUND

For localizing the origin(s) of cardiac arrhythmias it is common practice to measure the electric potentials located on the inner surface of the heart by electrophysiological means within the patient's heart. One method is to insert electrode catheters into the heart to record cardiac potentials during normal heart rhythm or cardiac arrhythmia. If the arrhythmia has a regular activation sequence, the timing of the electric activation measured in voltages at the site of the electrode can be accumulated when moving the electrode around during the arrhythmia, to create a three-dimensional map of the electric activation. By doing this, information on the localization of the source of arrhythmia(s) and mechanisms, i.e., re-entry circuits, can be diagnosed to initiate or guide treatment (radiofrequency ablation). The information can also be used to guide the treatment of cardiac resynchronization, in which implantable pacing electrodes are placed in specific locations within the heart wall or chambers to re-establish a normal level of coordinated activation of the heart.

A method using external sensors measures the electrical activity of the heart from the body surface using electrocardiographic techniques that include, for example, electrocardiograms (ECG) and vectorcardiography (VCG). These external sensor techniques can be limited in their ability to provide information and/or data on regional electrocardiac activity. These methods can also fail to localize bioelectric events in the heart.

A method using external sensors for the localization of cardiac arrhythmias utilizes body surface mapping. In this technique, multiple electrodes are attached to the entire surface of the thorax and the information of the cardiac electrograms (surface ECG) is measured in voltages that are accumulated into maps of cardiac activation. This measurement can be problematic because the electrical activity is time dependent and spatially distributed throughout the myocardium and also fails to localize bioelectric events in the heart. Complex mathematical methods are required to determine the electric activation upon the outer surface of a heart model (i.e. epicardium), for instance, one obtained from CT or MRI imaging giving information on cardiac size and orientation within the thoracic cavity.

Alternatively, recordings of potentials at locations on the torso, for example, can provide body surface potential maps (BSPMs) over the torso surface. Although the BSPMs can indicate regional cardiac electrical activity in a manner that can be different from conventional ECG techniques, these BSPM techniques generally provide a comparatively low resolution, smoothed projection of cardiac electrical activity that does not facilitate visual detection or identification of cardiac event locations (e.g., sites of initiation of cardiac arrhythmias) and/or details of regional activity (e.g., number and location of arrythmogenic foci in the heart).

Since the localization of cardiac arrhythmias by the use of potentials is imprecise, the successful treatment of cardiac arrhythmias has been difficult and has demonstrated limited success and reliability. There is, therefore, a need for improved methods of localizing, diagnosing and treating cardiac arrhythmias.

SUMMARY

In accordance with an aspect of the inventive concept, provided is a localization system, comprising: at least one catheter configured for delivery of one or more biopotential electrodes to a body cavity defined by surrounding tissue; a patient interface module comprising a plurality of localization electrodes configured for fixed orientation relative to the body; a cardiac information console configured to process localization signals from the localization electrodes to establish a manipulatable coordinate system for the tissue and to process the biopotential signals to orient the biopotential electrodes within the coordinate system.

In various embodiments, the cavity is a heart chamber and the surrounding tissue is one or more walls of the heart chamber.

In various embodiments, the one or more biopotential electrodes is a plurality of biopotential electrodes coupled to a distal end of the at least one catheter.

In various embodiments, the biopotential electrodes are disposed on a 3D array.

In various embodiments, the 3D array includes a plurality of splines.

In various embodiments, the 3D array is a basket array, a spiral array, a balloon, radially deployable arms, and/or other expandable and compactible structures.

In various embodiments, the patient interface module includes a patient isolation drive system, a set of patch electrodes, and one or more reference electrodes.

In various embodiments, the localization electrodes include one or more pairs of localization electrodes.

In various embodiments, the localization electrodes include two pairs of localization electrodes.

In various embodiments, each pair of localization electrodes defines an axis of the coordinate system.

In various embodiments, the localization electrodes include three pairs of localization electrodes, each pair of localization electrodes defining one axis of the coordinate system.

In various embodiments, a first pair of localization electrodes has two patch electrodes placed on opposite sides of the ribs; a second pair of localization electrodes has one patch electrode placed on the lower back and one patch electrode placed on the upper chest; and a third pair of localization electrodes has one patch electrode placed on the upper back and one patch electrode placed on the lower abdomen.

In various embodiments, the axes are non-orthogonal to a natural axis of the body.

In various embodiments, the pairs of localization electrodes are placed such that the axes intersect at an origin, and the origin is located in the heart.

In various embodiments, the origin of the three intersecting axes is centered on an atrial volume.

In various embodiments, the isolation drive system is configured to isolate the localization signals from the cardiac information console to prevent current leakage.

In various embodiments, the isolation drive system is configured to maintain simultaneous output on all axes generated by the localization electrode pairs.

In various embodiments, each pair of localization electrodes is driven by a different localization signal.

In various embodiments, each localization signal has a different frequency.

In various embodiments, the signals generated for the first pair of electrodes has a frequency of about 39 kHz; the signals generated for the second pair of electrodes has a frequency of about 48 kHz; and the signals generated for the third pair of electrodes has a frequency of about 52 kHz.

In various embodiments, the cardiac information console is further configured to rotate the coordinate system to adjust and correct an electronic representation of the 3D array of biopotentials.

In various embodiments, the cardiac information console is further configured to scale the coordinate system to adjust and correct an electronic representation of the 3D array of biopotentials.

In various embodiments, the cardiac information console is further configured to fit an electronic representation of the 3D array of biopotentials to a known or determined geometry of the 3D array of biopotentials.

In various embodiments, the system further comprises a user interface system configured to display the 3D array of biopotential electrodes and the coordinate system.

In various embodiments, the user interface system includes a mechanism that enables a user to rotate and/or scale the coordinate system to graphically adjust and correct an image of the 3D array of biopotentials.

In various embodiments, the cardiac information console further comprises, for each electrode, a biopotential signal path having a high impedance input and configured to receive biopotential signals from the biopotential electrodes; and/or a localization signal path having a high impedance input and configured to receive localization signals from the localization electrodes.

In various embodiments, the cardiac information console further comprises, for each electrode, a DFIB protection circuit coupled between the biopotential signal path and the localization signal path.

In various embodiments, the cardiac information console further comprises, for each electrode, an ADC coupled to outputs of the biopotential signal path and the localization signal path.

In various embodiments, the cardiac information console further comprises, coupled to an ADC output, a biopotential signal processor configured to provide cardiac activity mapping from processed biopotential data and a localization signal processor configured to localize the biopotential electrodes.

In various embodiments, the system further comprises an IQ demodulator, for each electrode, coupled to the output of the ADC and configured to separate the magnitude and phase of a received data signal; a narrow band IIR filter coupled to the IQ demodulator, and a time filter coupled to the IIR filter, and configured to selectively filter out portions of data on a time basis.

In various embodiments, there is one IIR filter, comprising an I portion and a Q portion, for each IQ demodulator.

In various embodiments, there is one multichannel IIR filter for a plurality of IQ demodulators.

In various embodiments, the system further comprises one or more auxiliary catheters.

In various embodiments, the one or more auxiliary catheters comprises at least one of an ablation catheter or a reference catheter.

In various embodiments, the at least one catheter further includes ultrasound electrodes configured to collect image data to generate one or more images of the tissue.

In various embodiments, the cardiac information console further comprises an ultrasound signal path having a high impedance input and configured to receive ultrasound signals from the ultrasound electrodes.

In various embodiments, the system comprises one or more sensors configured to produce one or more signals indicating a presence of, an absence of, and/or a change in at least one sensed condition.

In various embodiments, the one or more sensors comprises at least one catheter sensor.

In various embodiments, the at least one catheter sensor comprises a sensor mounted to or integral with: a catheter handle of the at least one catheter and/or a catheter array coupled to a distal end of the at least one catheter.

In various embodiments, the at least one catheter sensor comprises a patient physiologic sensor selected from the group consisting of: a blood pressure sensor; a blood gas sensor; a temperature sensor; a blood glucose sensor; a pH sensor; a respiration sensor; an average clotting time (ACT) sensor; and combinations of one or more of these.

In various embodiments, the one or more sensors comprises at least one cardiac information console sensor.

In various embodiments, the one or more sensors comprises at least one patient interface system sensor.

In various embodiments, the one or more sensors comprises a plurality of sensors, including at least two sensors selected from the group consisting of: a catheter sensor; a cardiac information console sensor; a patient interface system sensor; and combinations of one or more these.

In various embodiments, the one or more sensors comprise at least one sensor selected from the group consisting of: a force sensor; a pressure sensor; a strain gauge; an optical sensor; an imaging sensor; a sound sensor; a hall effect sensor; a pH sensor; a magnetic sensor; a temperature sensor; and combinations of one or more of these.

In various embodiments, the imaging sensor includes a lens and/or optical fiber.

In various embodiments, the sound sensor includes a ultrasound sensor.

In various embodiments, the one or more of sensors comprise at least one transducer selected from the group consisting of: a heating element; a cooling element; a vibrating element; a drug or other agent delivery element; a magnetic field generating element; a light delivery element; an imaging element; and combinations of one or more of these.

In various embodiments, the imaging element includes a lens and/or optical fiber.

In various embodiments, the system is configured to analyze the one or more signals produced by the one or more sensors.

In various embodiments, the system is configured to perform an analysis of one or more signals produced by the one or more of sensors in combination with voltage data, dipole density data, surface charge data, and/or anatomical data sensed and/or calculated by the system.

In various embodiments, the one or more signals from the one or more sensors are used by system to perform a function selected from the group consisting of: improve an anatomical image displayed by system; improve cardiac information displayed by system (e.g. dipole density and/or surface charge information); detect a malfunction of system; provide physiologic data of a patient; and combinations of one or more of these.

In various embodiments, the cardiac information displayed by system includes at least one of dipole density information and/or surface charge information.

In accordance with another aspect of the inventive concept, provided is a localization method, comprising: delivering one or more biopotential electrodes to a body cavity defined by surrounding tissue using at least one catheter; receiving biopotential signals from the one or more biopotential electrodes; establishing a manipulatable coordinate system for the tissue using localization electrodes having a fixed orientation relative to the body; and processing the biopotential signals to orient and/or reorient the biopotential electrodes within the coordinate system.

In various embodiments, the cavity is a heart chamber and the surrounding tissue is one or more walls of the heart chamber.

In various embodiments, the one or more biopotential electrodes is a plurality of biopotential electrodes coupled to a distal end of the at least one catheter.

In various embodiments, the biopotential electrodes are disposed on a 3D array.

In various embodiments, the 3D array includes a plurality of splines.

In various embodiments, the 3D array is a basket array, spiral array, a balloon, radially deployable arms, and/or other expandable and compactible structures.

In various embodiments, the localization electrodes include a set of patch electrodes and one or more reference electrodes.

In various embodiments, the localization electrodes include one or more pairs of localization electrodes.

In various embodiments, the localization electrodes include two pairs of localization electrodes.

In various embodiments, each pair of localization electrodes defines an axis of the coordinate system.

In various embodiments, the localization electrodes include three pairs of localization electrodes, each pair of localization electrodes defining one axis of the coordinate system.

In various embodiments, a first pair of localization electrodes has two patch electrodes placed on opposite sides of the ribs, a second pair of localization electrodes has one patch electrode placed on the lower back and one patch electrode placed on the upper chest, and a third pair of localization electrodes has one patch electrode placed on the upper back and one patch electrode placed on the lower abdomen.

In various embodiments, the axes are non-orthogonal to a natural axis of the body.

In various embodiments, the pairs of localization electrodes are placed such that the axes intersect at an origin, and the origin is located in the heart.

In various embodiments, the origin of the three intersecting axes is centered on an atrial volume.

In various embodiments, the method further comprises maintaining simultaneous output on all axes generated by the localization electrode pairs.

In various embodiments, the method further comprises driving each pair of localization electrodes with a different localization signal.

In various embodiments, each localization signal has a different frequency.

In various embodiments, the method further comprises generating the signals for the first pair of electrodes at a frequency of about 39 kHz; generating the signals for the second pair of electrodes at a frequency of about 48 kHz; and generating the signals for the third pair of electrodes at a frequency of about 52 kHz.

In various embodiments, receiving biopotential signals from the one or more biopotential electrodes includes: using at least one processor, rotating the coordinate system to adjust and correct an electronic representation of a 3D array of biopotentials sensed and/or recorded by the one or more biopotential electrodes.

In various embodiments, the method further comprises using at least one processor, scaling the coordinate system to adjust and correct an electronic representation of the 3D array of biopotentials.

In various embodiments, the method further comprises fitting an electronic representation of the 3D array of biopotentials to a known or determined geometry of the 3D array of biopotentials.

In various embodiments, the method further comprises displaying the 3D array of biopotential electrodes and the coordinate system on at least one display of a user interface system.

In various embodiments, the method further comprises rotating and/or scaling the coordinate system to graphically adjust and correct an image of the 3D array of biopotentials in response to user interaction with the user interface system.

In various embodiments, processing the biopotential signals includes: receiving I and Q data based on the receiving biopotential signals; converting the IQ data to voltage data; applying an axis correction factor to the voltage data, based on a known and/or measured shape of the electrode array; determining a scaling matrix and applying the scaling matrix to the sensed voltage data, based on a known and/or measured shape of the electrode array; calculating position values of each electrode, each electrode having a corrected voltage value based on the axis correction and scaling of the voltage data; and fitting the calculated position values of each electrode to a known basket configuration.

In various embodiments, the method further comprises applying fitting and rotations to the calculated electrode positions; and updating the electrode positions.

In various embodiments, the method further comprises, if a next set of biopotential data exists, repeating the method for the next set of biopotential data.

In various embodiments, the localization electrodes include a plurality of pairs of localization electrodes and there are is one axis for each pair of localization electrodes, and the method comprises rotating, scaling and/or deskewing one or more of the axes until the electrode array takes a predetermined shape.

In various embodiments, the electrode array is a 3D basket array.

In various embodiments, the method further comprises displaying the electrode array on a display of a user interface subsystem.

In various embodiments, applying the scaling matrix comprises, if a length or a size of the electrode array is incorrect, based on known or determined proportions of the electrode array, scaling one or more of the axes of the electrode array longer or shorter until the known or determined proportions of the electrode array is/are achieved.

In various embodiments, the method further comprises, for each electrode: receiving biopotential signals from the biopotential electrodes via a biopotential signal path having a high impedance input; and/or receiving localization signals from the localization electrodes via a localization signal path having a high impedance input.

In various embodiments, the method further comprises, for each electrode: coupling a DFIB protection circuit between the biopotential signal path and the localization signal path.

In various embodiments, the method further comprises, for each electrode: coupling outputs of the biopotential signal path and the localization signal path to an ADC.

In various embodiments, the method further comprises coupling a biopotential signal processor and a localization signal processor to an ADC output; providing cardiac activity mapping from processed biopotential data using the biopotential signal processor; and localizing the biopotential electrodes using the localization signal processor.

In various embodiments, the method further comprises for each electrode, coupling an IQ demodulator to the output of the ADC and separating a magnitude and a phase of a received biopotential signals; coupling a narrow band IIR filter to the IQ demodulator; and coupling a time filter to the IIR filter, and selectively filtering out portions of data on a time basis.

In various embodiments, there is one IIR filter, comprising an I portion and a Q portion, for each IQ demodulator.

In various embodiments, there is one multichannel IIR filter for a plurality of IQ demodulators.

In various embodiments, the method further comprises delivering one or more auxiliary catheters to the body cavity.

In various embodiments, the one or more auxiliary catheters comprises at least one of an ablation catheter or a reference catheter.

In various embodiments, the at least one catheter further includes ultrasound electrodes, and the method includes collecting image data from the ultrasound electrodes to generate an image of the tissue.

In various embodiments, the method further comprises receiving ultrasound signals from the ultrasound electrodes via an ultrasound signal path having a high impedance input.

In accordance with aspects of the inventive concept, provided is a localization method as shown and/or described.

In accordance with aspects of the inventive concept, provided is a localization system as shown and/or described.

In accordance with aspects of the inventive concept, provided is a cardiac information processing system as shown and/or described.

DETAILED DESCRIPTION

Figure 1:
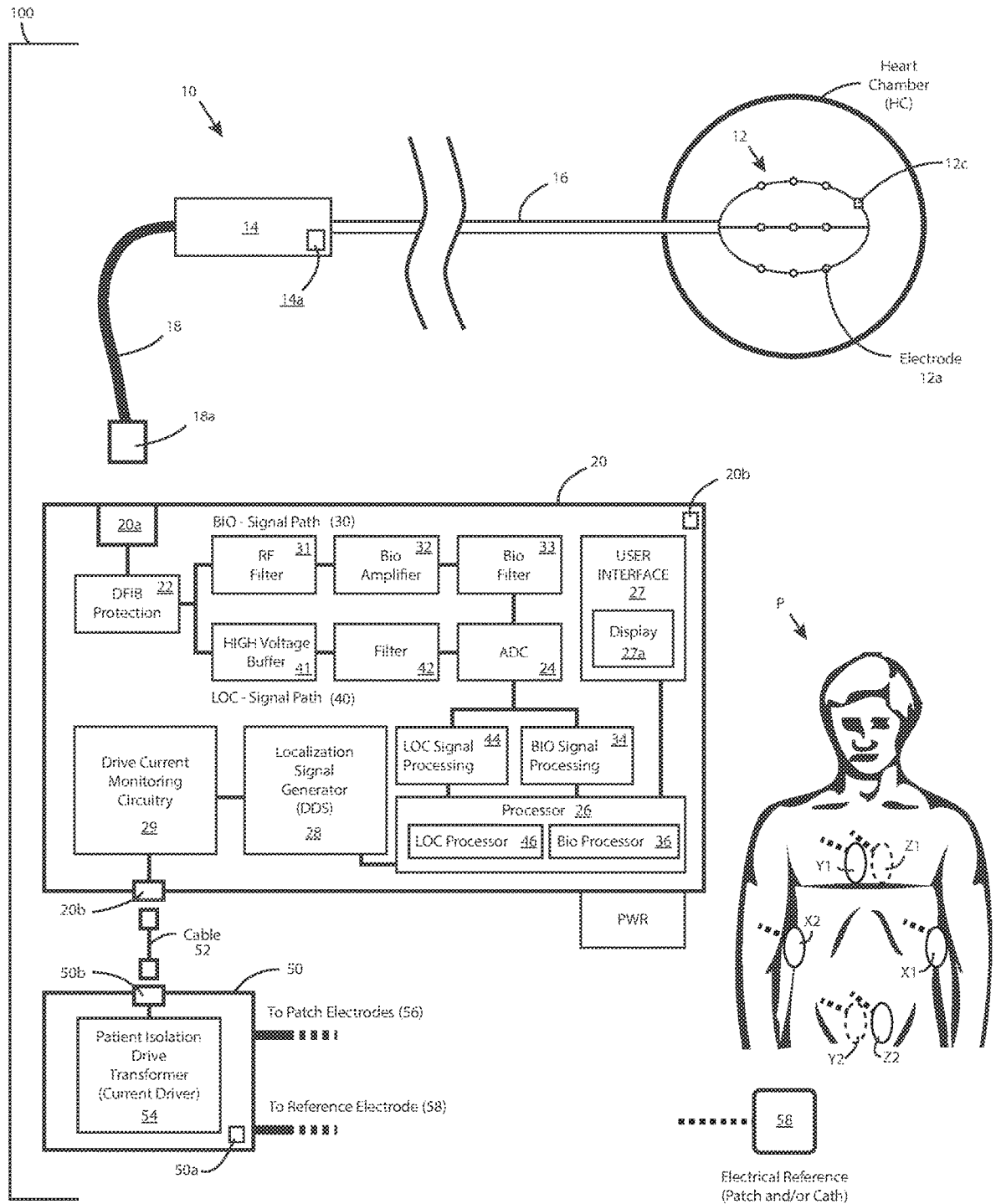
FIG. 1 provides a block diagram of an embodiment of a cardiac information processing system, in accordance with aspects of the inventive concept.

Various exemplary embodiments will be described more fully hereinafter with reference to the accompanying drawings, in which some exemplary embodiments are shown. The present inventive concept can, however, be embodied in many different forms and should not be construed as limited to the exemplary embodiments set forth herein.

It will be understood that, although the terms first, second, etc. are used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items. And a "combination" of associated listed items need not include all of the items listed, but can include all of the items listed.

It will be understood that when an element is referred to as being "on" or "attached", "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like can be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

Various exemplary embodiments are described herein with reference illustrations of idealized or representative structures and intermediate structures. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

Referring now to FIG. 1, provided is a block diagram of an embodiment of a cardiac information processing system 100, in accordance with aspects of the inventive concept. The cardiac information processing system 100 can be or include a system configured to perform cardiac mapping, diagnosis, and/or treatment, such as for treating abnormalities such as arrhythmia. Additionally or alternatively, the system can be a system configured for teaching and or validating devices and methods of diagnosing and/or treating cardiac abnormalities or disease of a patient P.

The cardiac information processing system 100 includes a catheter 10, a cardiac information console 20, and a patient interface module 50 that can be configured to cooperate to accomplish the various functions of the cardiac information processing system 100. Preferably, cardiac information processing system 100 includes a single power supply (PWR), which can be shared by the cardiac information console 20 and the patient interface module 50. Unlike typical systems, use of a single power supply in this way can greatly reduce the chance for leakage currents to propagate into the patient interface module 50 and cause errors in localization.

The catheter 10 includes an electrode array 12 that can be percutaneously delivered to a heart chamber (HC). The array of electrodes has a known spatial configuration. For example, in the expanded state the physical relationship of the electrodes can be known or reliably assumed. Diagnostic catheter 10 also includes a handle 14, and an elongate flexible shaft 16 extending from handle 14. Attached to the distal end of shaft 16 is the electrode array 12, such as a 3D array in the form of a radially expandable and/or compactible assembly. In this embodiment, the electrode array 12 is shown as a basket array, but the electrode array could take other forms in other embodiments. In some embodiments, expandable electrode array 12 is constructed and arranged as described in reference to applicant's co-pending Patent Cooperation Treaty Patent Application Serial Number PCT/US2013/057579, titled "System and Method for Diagnosing and Treating Heart Tissue", filed Aug. 30, 2013, the content of which is incorporated herein by reference by its entirety. In other embodiments, expandable electrode array 12, as a 3D array, can comprise a balloon, radially deployable arms, spiral, and/or other expandable and compactible structure.

Shaft 16 and expandable electrode array 12 are constructed and arranged to be inserted into a body (e.g. an animal body or a human body, such as the body of Patient P), and advanced through a body vessel, such as a femoral vein or other blood vessel. Shaft 16 and electrode array 12 can be constructed and arranged to be inserted through an introducer (not shown), such as when electrode array 12 is in a compacted state, and slidingly advanced through a lumen of a shaft into a body space, such as a chamber of the heart (HC), such as the right atrium or the left atrium, as examples.

Expandable electrode array 12 can further comprise multiple splines, each spline having a plurality of electrodes 12a. Three splines are visible in FIG. 1, but the basket array is not limited to three splines; more or less splines can be included in the basket array. Each electrode 12a can be configured to record a voltage, such as the voltage present on a surface of the heart or at a location within a heart chamber HC. As a non-limiting example, the three electrodes 12a are shown on each spline in this embodiment. However, in other embodiments the basket array can include more or less electrodes.

Catheter 10 can comprise a cable or other conduit, such as cable 18, configured to electrically, optically, and/or electro-optically connect catheter 10 to the cardiac information console 20 via connectors 18a and 20a, respectively.

The patient interface module 50 can be configured to electrically isolate one or more components of the cardiac information console 20 from patient P (e.g., to prevent undesired delivery of a shock or other undesired electrical energy to patient P). The patient interface module 50 can be integral with cardiac information console 20 and/or it can comprise a separate discrete component (e.g. separate housing), as is shown. The cardiac information console 20 comprises one or more connectors 20b, each comprising a jack, plug, terminal, port, or other custom or standard electrical, optical, or electro-optical connector. Similarly, the patient interface module 50 includes one or more connectors 50b. At least one cable 52 connects the patient interface module 50 with the cardiac information console 20, via connectors 20b and 50b.

The patient interface module 50 includes a patient isolation drive system 54 and a set of localization electrodes. In this embodiment, the set of localization electrodes includes a set of patch electrodes 56 and one or more reference electrode 58. The isolation drive system 54 isolates localization signals from the rest of system to prevent current leakage, e.g., signal loss—resulting in performance degradation. The isolation drive system 54 can minimize drift in localization positions and maintain a high isolation between axes. Additionally, the isolation drive system 54 maintains simultaneous output on all axes, while also increasing the sampling rate at each electrode position. In some embodiments, the sampling rate comprises a rate between 10 kHz and 1 MHz, such as a sampling rate of approximately 625 kHz.

In this embodiment, the set of patch electrodes 56 include three (3) pairs of patch electrodes: an "X" pair having two patch electrodes placed on opposite sides of the ribs (X1, X2); a "Z" pair having one patch electrode placed on the lower back (Z1) and one patch electrode placed on the upper chest (Z2); and a "Y" pair having one patch electrode placed on the upper back (Y1) and one patch electrode placed on the lower abdomen (Y2). The patch electrode 56 pairs can be placed on any orthogonal and/or non-orthogonal sets of axes. In the embodiment of FIG. 1, the placement of electrodes is shown on patient P, where electrodes on the back are shown in dashed lines.

The placement of electrodes 56 defines a coordinate system made up of three axes, one axis per pair of patch electrodes 56. In some embodiments, the axes are non-orthogonal to a natural axis of the body: head-to-toe, chest-to-back, and side-to-side (i.e., rib-to-rib). The electrodes can be placed such that the axes intersect at an origin, such as an origin located in the heart. For instance, the origin of the three intersecting axes can be centered in an atrial volume. System 100 can be configured to provide an "electrical zero" that is positioned outside of the heart, such as by locating a reference electrode 58 such that the resultant electrical zero is outside of the heart (e.g. to avoid crossing from a positive voltage to a negative voltage at a location being localized).

Through processing by the cardiac information console 20, the axes can be rotated from the normal physiological orientation, i.e., anterior-posterior, cranial-caudal, left-right. Rotated axes provide improved spatial resolution. Once the desired rotation is achieved, each axis can be scaled, i.e., made longer or shorter, as needed. The rotation and scaling are performed based on comparing expected or known electrode array 12 shape and relative dimensions with a representation of the electrode array in the patch electrode established coordinate system. In such a case, rotation and scaling is performed to bring an incorrect representation into a more accurate representation. Therefore, shaping and scaling the representation of the electrode array 12 serves to adjust and correct the orientation and relative sizes of the axes for far more accurate localization.

The reference electrode(s) 58 can be or include a patch electrode and/or an electrical reference catheter, as a patient reference. A patch electrode can be placed on the skin, and will act as a return for current for defibrillation. An electrical reference catheter can include a unipolar reference electrode used in baseline and restore functions, and can be used for common mode rejection. Another form of electrical reference catheter can be an internal analog reference electrode, which can act as a low noise "analog ground" for all internal catheter electrodes. Each of these types of reference electrodes can be placed in relatively similar locations, such as near lower back in internal vessel (as a catheter) and/or on lower back (as a patch). In some embodiments, system 100 comprises a reference catheter 58 including a fixation mechanism (e.g. a user activated fixation mechanism), which can be constructed and arranged to reduce displacement (e.g. accidental or otherwise unintended movement) of one or more electrodes of the reference catheter 58. The fixation mechanism can comprise a mechanism selected from the group consisting of: spiral expander; spherical expander; circumferential expander; axially actuated expander; rotationally actuated expander; and combinations of two or more of these.

In FIG. 1, aspects of the receiver components of the cardiac information console 20 are depicted. The cardiac information console 20 includes an input defibrillation protection module 22 connected to connector 20a, which is configured to receive cardiac information from the catheter 10. The DFIB protection module 22 is configured to have a precise clamping voltage and a minimum capacitance. Functionally, the DFIB protection module 22 acts a surge protector.

The DFIB protection module 22 is coupled to two signal paths, a biopotential (BIO) signal path 30 and a localization (LOC) signal path 40. Generally, the BIO path 30 filters noise and preserves the measured biopotential data, and also enables the biopotential signals to be read while ablating, which is not the case in other systems. Generally, the LOC path 40 allows high voltage inputs, while filtering noise from received localization data.

The BIO signal path 30 includes an RF filter 31 coupled to the DFIB protection module 22. In this embodiment, the RF filter 31 operates as a low-pass filter having a high input impedance. The high input impedance is preferred in this embodiment because it minimizes the loss of voltage from the source, e.g., catheter 10, thereby better preserving the received signals. The RF filter 31 is configured to allow biopotential signals from the electrodes 12a on catheter 10 to pass, e.g., frequencies less than 500 Hz, such as frequencies in the range of 0.1 Hz to 500 Hz. However, high voltages, such as from ablation, are filtered out from the biopotential signal path 30. RF filter 31 can comprise a bandwidth between 10 kHz and 12 kHz.

A BIO amplifier 32 is preferably a low noise single-ended input amplifier that amplifies the RF filtered signal. A BIO filter 33 filters noise out of the amplified signal. BIO filter 33 can comprise an approximately 3 kHz filter. In some embodiments, BIO filter 33 comprises an approximately 7.5 kHz filter, such as when system 100 is configured to accommodate pacing of the heart (e.g. avoid significant signal loss and/or degradation during pacing of the heart).

The LOC signal path 40 includes a high voltage buffer 41 coupled to the DFIB protection module 22. In this embodiment, the high voltage buffer 41 is configured to accommodate the relatively high RF voltages used in treatment techniques, such as RF ablation. For example, the high voltage buffer can have ±100 voltage rails. The high voltage buffer 41 also has a high input impedance, such as when the high voltage buffer 41 does not include a pre-filter stage, and has good performance at high frequencies. A high frequency bandpass filter 42 is coupled to the high voltage buffer 41, and has a passband frequency range of about 20 kHz to 80 kHz for use in localization. Preferably, the filter 42 has low noise with good gain, e.g., a gain of 1.

An AD (analog-to-digital) converter ADC 24 is coupled to the BIO filter 33 of the BIO signal path 30 and to the high frequency filter 42 of the LOC signal path 40. The ADC 24 has high oversampling to allow noise shaping and filtering, e.g., with an oversampling rate of about 625 kHz. In some embodiments, sampling is performed at or above the Nyquist frequency of system 100. The ADC 24 is a multi-channel circuit that can combine BIO and LOC signals or keep them separate. In one embodiment, as a multi-channel circuit, the ADC 24 can be configured to accommodate 48 biopotential electrodes 12a and 32 auxiliary electrodes (e.g., for ablation or other processes), for a total of 80 channels. In other embodiments, more or less channels can be provided. In FIG. 1, for example, almost all of the elements of the cardiac information console 20 can be duplicated for each channel, e.g., except for the UI system 27. For example, the cardiac information console 20 can include a separate ADC for each channel, or an 80 channel ADC.

Consistent with the two different signals and signal paths 30, 40, signal information from each path is input to and output from the various channels of the ADC 24. Outputs from the channels of the ADC 24 are coupled to either the BIO signal processing module 34 or the LOC signal processing module 44, which pre-process their respective signals for subsequent processing as described herein below. In each case, the preprocessing prepares the received signals for the processing by their respective dedicated processors discussed below. The BIO signal processing module 34 and the LOC signal processing module 44 can be implemented in firmware, in whole or in part, in some embodiments.

The biopotential signal processing module 34 can provide gain and offset adjustment and digital RF filtering having a non-dispersive low pass filter and intermediate frequency band. The intermediate frequency band can eliminate ablation and localization signals. Additionally, the biopotential signal processing can also include pace blanking, which is the blanking of received information during a timeframe when, for example, a physician is "pacing" the heart. Cardiac pacing is applied clinically by standard means. The pacing may be used to temporarily alter the heart rhythm, trigger the heart beat from specific locations on the cardiac wall, or for checking the health of the cardiac tissue by looking at propagation velocities of the pacing pulses.

To accomplish the foregoing, active and passive pacing trigger and input algorithmic trigger determination can be performed. The algorithmic trigger determination can use subsets of channels, edge detection and/or pulse width detection to determine if pacing has occurred. The biopotential signal processing module 34 can also include digital biopotential filtering, which can be a non-dispersive low pass filter with an optimized output sample rate.

The localization signal processing module 44 can provide individual channel/frequency gain calibration, IQ demodulation with tuned demodulation phase, synchronous and continuous demodulation (no MUXing), narrow band IIR filtering, and time filtering (Interleaving, blanking, etc.), as discussed herein below.

A data processor 26, which may include one or more of a plurality of types of processing circuits (e.g., a microprocessor) and memories, executes computer instructions necessary to perform the processing of the pre-processed signals from the BIO signal processing module 34 and localization signal processing module 44. The data processor 26 can be configured to perform calculations, as well as perform data storage and retrieval, necessary to perform the functions of the cardiac information processing system 100.

In this embodiment, data processor 26 includes a biopotential (Bio) processor 36 and a localization (LOC) processor 46. The biopotential processor 36 can perform processing of measured biopotentials. The LOC processor 46 can perform processing of localization signals.

The biopotential processor 36 can be configured to perform various calculations. For example, the BIO processor 36 can include an enhanced common mode rejection filter, which can be bidirectional to minimize distortion and which may be seeded with a common mode signal. The BIO processor 36 can also include an optimized ultrasound rejection filter and be configured for selectable bandwidth filtering.

The localization processor 46 can be configured to perform various calculations. As discussed in more detail below, the LOC processor 46 can electronically make (calculate) corrections to an axis based on the known shape of electrode array 12, make corrections to scaling of one or more axis based on the known shape of the electrode array 12, and perform "fitting" to align measured electrode positions with known possible configurations, which can be optimized with one or more constraints (e.g. physical constraints such as distance between two electrodes 12a on a single spline, distance between two electrodes 12a on two different splines, maximum distance between two electrodes 12a; minimum distance between two electrodes 12a, minimum and/or maximum curvature of a spine).

The cardiac information console 20 also includes localization driving circuitry, including a localization signal generator 28 and a localization drive current monitor circuit 29. The localization driving circuitry provides high frequency localization drive signals (e.g., 10 kHz-1 MHz, such as 10 kHz-100 kHz). Localization using drive signals at these high frequencies reduces the cellular response effect on the localization data, e.g., from blood cell deformation, and/or allow higher drive currents, e.g., to achieve a better signal-to-noise ratio. The signal generator 28 produces a high resolution digital synthesis of a drive signal, e.g., sine wave, with ultra-low phase noise timing. The drive current monitoring circuitry provides a high voltage, wide bandwidth current source, which is monitored to measure impedance of the patient P.

The cardiac information console 20 can also include a user interface (UI) subsystem 27 configured to output results of the localization and biopotential processing. The UI subsystem 27 can include at least one display 27a to graphically render such results in 2D, 3D, or a combination thereof. The user interface system 27 can include one or more mechanisms that enable a user to rotate and/or scale the coordinate system to graphically adjust and correct an image of the 3D array of biopotentials. Such mechanisms can include a touchscreen, mouse, keyboard, light pen, track ball, microphone, and so on.

In some embodiments, system 10 comprises one or more sensors, each configured to produce a signal, a sensor of catheter 10 (e.g. sensor 14a of handle 14 or sensor 12c of array 12), a sensor 20b of cardiac information console 20 and/or a sensor 50a of patient interface module 50, each as shown in FIG. 1. In some embodiments, system 10 comprises two or more of sensors 12c, 14a, 20b, and/or 50a. In some embodiments, sensors 12c, 14a, 20b, and/or 50a comprise a sensor selected from the group consisting of: a force sensor; a pressure sensor; a strain gauge; an optical sensor; an imaging sensor (e.g. a lens or optical fiber); a sound sensor such as an ultrasound sensor; a hall effect sensor; a pH sensor; a magnetic sensor; a temperature sensor; and combinations of one or more of these. In some embodiments, sensor 12c comprise a patient physiologic sensor, such as a sensor selected from the group consisting of: a blood pressure sensor; a blood gas sensor; a temperature sensor; a blood glucose sensor; a pH sensor; a respiration sensor; an average clotting time (ACT) sensor; and combinations of one or more of these. In some embodiments, system 10 is configured to analyze a signal produced by one, two or more of sensors 12c, 14a, 20b, and/or 50a. In some embodiments, system 10 (e.g. cardiac information console 20) is configured to perform an analysis of one or more signals produced by one, two or more of sensors 12c, 14a, 20b, and/or 50a in combination with voltage data, dipole density data, surface charge data, and/or anatomical data (e.g. anatomical data collected by one or more ultrasound transducers 133). In some embodiments, signals from one or more sensors 12c, 14a, 20b, and/or 50a are used by system 10 to perform a function selected from the group consisting of: improve an anatomical image displayed by system 10; improve cardiac information displayed by system 10 (e.g. dipole density and/or surface charge information); detect a malfunction of system 10; provide physiologic data of a patient; and combinations of one or more of these. In some embodiments, one or more of sensors 12c, 14a, 20b, and/or 50a can comprise a transducer (e.g. as an alternative to being a sensor or in addition to being a sensor), such as a transducer selected from the group consisting of: a heating element; a cooling element; a vibrating element; a drug or other agent delivery element; a magnetic field generating element; a light delivery element; an imaging element (such as a lens, and/or optical fiber); and combinations of one or more of these.

Figure 2:
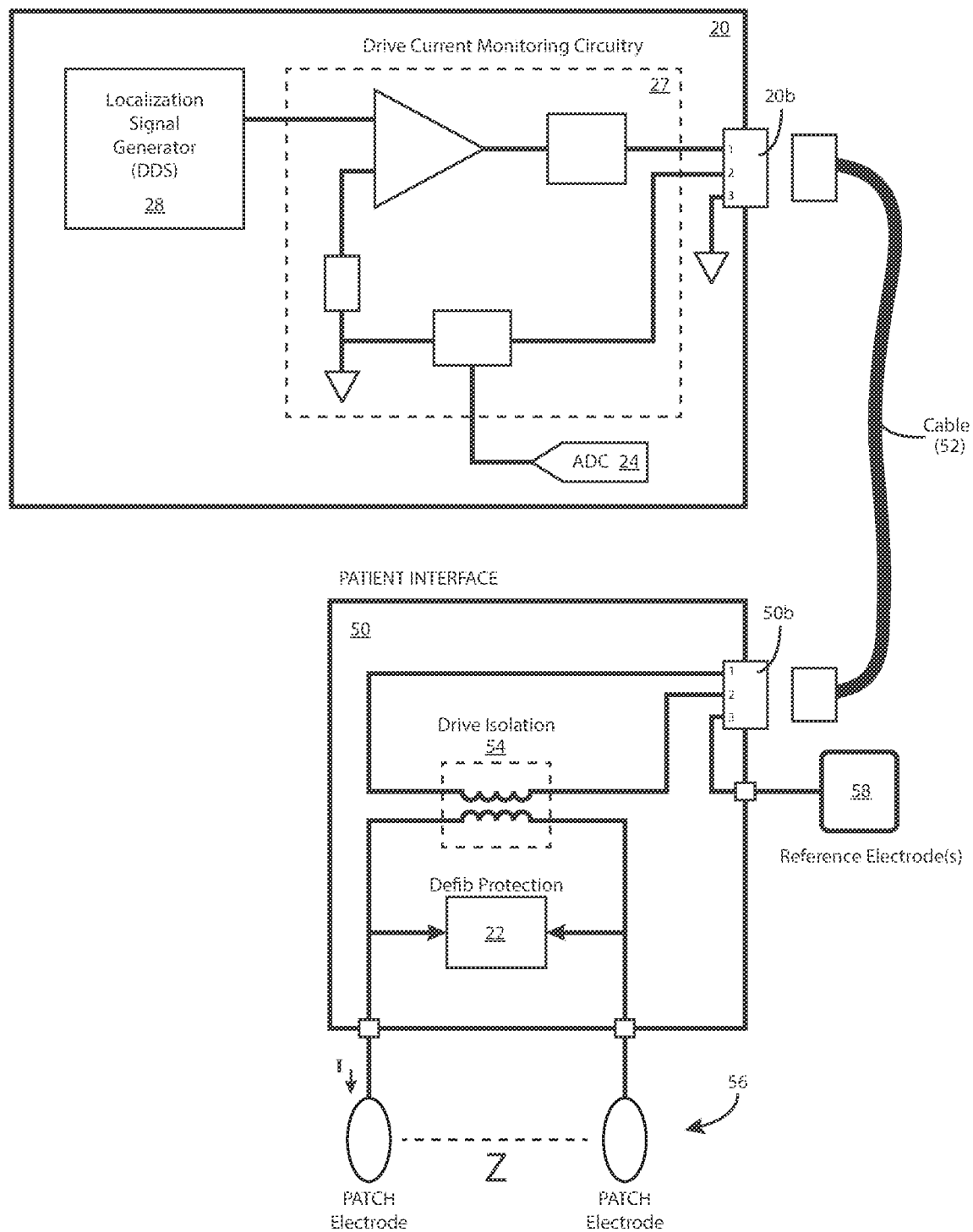
FIG. 2 provides a circuit diagram of an embodiment of the localization driving circuitry and UI system of FIG. 1.

FIG. 2 provides a circuit diagram of an embodiment of the localization driving circuitry and UI system of FIG. 1. FIG. 2 shows portions of the UI subsystem 27, the localization signal generator 28, and the localization drive current monitor circuit 29 of FIG. 1.

The localization signal generator 28 is a DDS (Direct Digital Synthesizer) that generates waveforms for localization, such as sine waves. One waveform is generated per "axis," currently a 3 axes system. High frequency sine waves are generated for each axis, such as 3 sine waves at different frequencies. For example, the signals generated for the X pair of electrodes can be at 39 kHz; the signals generated for the Y pair of electrodes can be at 48 kHz; and the signals generated for the Z pair of electrodes can be at 52 kHz.

The drive current monitoring circuitry 29 provides a feedback system for monitoring and maintaining current delivered by the localization system to the patient P, using the ADC as an output. The drive current monitoring circuitry 29 can monitor current output and determine physical parameters of the system, such as impedance of the body, issues with patch placement, changes in physical parameters, and/or hardware error and/or failure.

In this embodiment, the cardiac information console 20 and patient interface module 50 share a common ground, through use of a single power source. As shown, the patient interface module 50 provides localization driver isolation using a transformer. This provides better isolation, while driving different pairs of electrodes, e.g., currently 3 pairs of electrodes are simultaneously driven with 3 different frequencies.

In FIG. 2, the impedance between two electrodes in a pair of electrodes is indicated by "Z" (the customary symbol for impedance).

Figure 3:
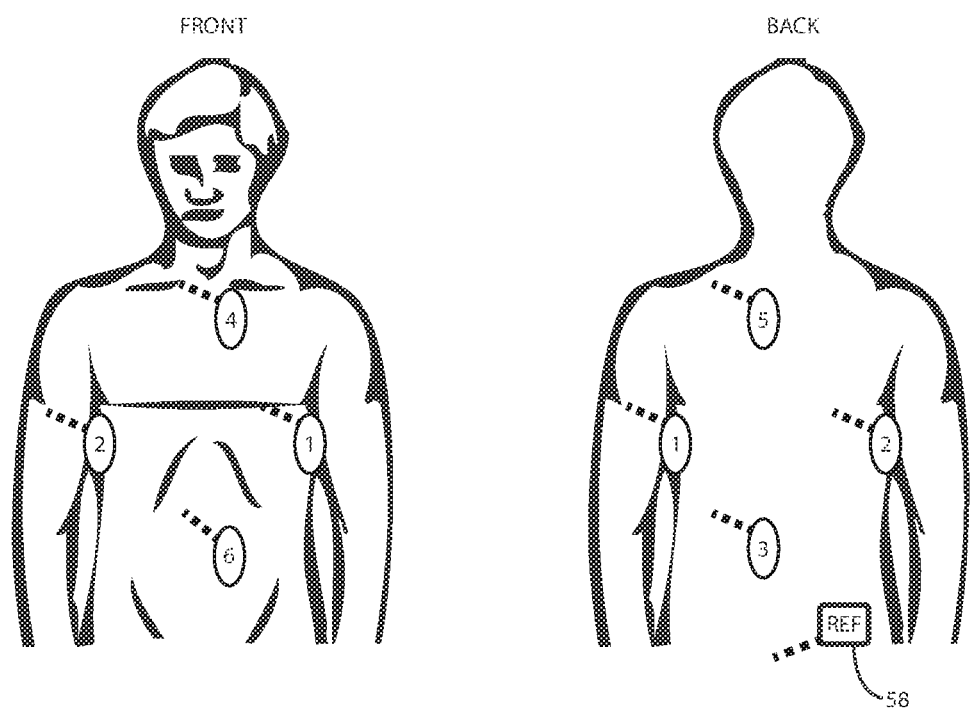
FIG. 3 is a drawing providing a front view and a back view of a patient and relative electrode placement, in accordance with aspects of the inventive concept.

FIG. 3 is a drawing providing a front view and a back view of a patient and relative electrode placement, in accordance with aspects of the inventive concept. This figure demonstrates a preferred patch electrode placement, as discussed above. In FIG. 1, for example, the X electrodes X1 and X2 are shown as patch electrodes 1 and 2, respectively; the Z electrodes Z1 and Z2 are shown as patch electrodes 3 and 4, respectively; and the Y electrodes Y1 and Y2 are shown as patch electrodes 5 and 6, respectively. Thus, patches 1 and 2 are placed on the ribs, forming X axis within the body; patches 3 and 4 are placed on the lower back and upper chest (respectively), forming the Z axis; and patches 5 and 6 are placed on the upper back and lower abdomen (torso) (respectively), forming the Y Axis. The three axis are of similar length, and not aligned with "natural" axis of the body (i.e., head to toe, chest to back, and side to side).

The reference patch electrode 58 can be placed on the lower back/buttocks. Additionally, or alternatively, a reference catheter can be placed in similar location within a body vessel.

As described hereabove, a patch pair can operate differentially, i.e. neither patch 56 in a pair operates as a reference electrode, and are both driven by system 100 to generate the electrical field between the two. Alternatively or additionally, one or more of the patch electrodes 56 can serve as the reference electrode 58, such that they operate in a single ended mode. One of any pair of patch electrodes 56 can serve as the reference electrode 58 for that patch pair, forming a single-ended patch pair. One or more patch pairs can be configured to be independently single-ended. One or more of the patch pairs can share a patch as a single-ended reference or can have the reference patches of more than one patch pair electrically connected.

Through processing performed by the cardiac information console 20, the axes can be transformed, e.g., rotated, from a first orientation, e.g., a non-physiological orientation based on the placement of electrodes 56, to a second orientation. The second orientation can comprise a standard Left-Posterior-Superior (LPS) anatomical orientation, i.e., the "x" axis is oriented from right to left of the patient, the "y" axis is oriented from the anterior to posterior of the patient, and the "z" axis is oriented from cauda to cranial of the patient. Placement of patch electrodes 56 and the non-standard axes defined thereby can be selected to provide improved spatial resolution when compared to patch electrode placement resulting in a normal physiological orientation of the resulting axes, e.g. due to preferred tissue characteristics between electrodes 56 in the non-standard orientation. For example, non-standard electrode placement can result in diminished influence of the low-impedance volume of the lungs on the localization field. Furthermore, electrode placement can be selected to create axes which pass through the body of the patient along paths of similar or equivalent lengths. Axes of similar length will possess more similar energy density per unit distance within the body, yielding a more uniform spatial resolution along such axes. Transforming the non-standard axes into a standard orientation can provide a more straightforward display environment for the user. Once the desired rotation is achieved, each axis can be scaled, i.e., made longer or shorter, as needed. The rotation and scaling are performed based on comparing pre-determined, e.g., expected or known, electrode array 12 shape and relative dimensions, with measured values that correspond to the shape and relative dimensions of the electrode array in the patch electrode established coordinate system. For example, rotation and scaling can be performed to transform a relatively inaccurate, e.g., uncalibrated, representation into a more accurate representation. Shaping and scaling the representation of the electrode array 12 can adjust, align, and/or otherwise improve the orientation and relative sizes of the axes for far more accurate localization.

The reference electrode(s) 58 can be or include a patch electrode and/or an electrical reference catheter, as a patient reference. A patch electrode 58 can be placed on the skin, and will act as a return for current for defibrillation. An electrical reference catheter can include a unipolar reference electrode used to enhance common mode rejection. The unipolar reference electrode, or other electrodes on a reference catheter, can be used to measure, track, correct, or calibrate physiological, mechanical, electrical, or computational artifacts in a cardiac signal. In some embodiments, these artifacts may be due to respiration, cardiac motion, or artifacts induced by applied signal processing, such as filters. Another form of electrical reference catheter can be an internal analog reference electrode, which can act as a low noise "analog ground" for all internal catheter electrodes. Each of these types of reference electrodes can be placed in relatively similar locations, such as near the lower back in an internal vessel (as a catheter) and/or on the lower back (as a patch). In some embodiments, system 100 comprises a reference catheter 58 including a fixation mechanism (e.g. a user activated fixation mechanism), which can be constructed and arranged to reduce displacement (e.g. accidental or otherwise unintended movement) of one or more electrodes of the reference catheter 58. The fixation mechanism can comprise a mechanism selected from the group consisting of: spiral expander; spherical expander; circumferential expander; axially actuated expander; rotationally actuated expander; and combinations of two or more of these.

Figure 4:
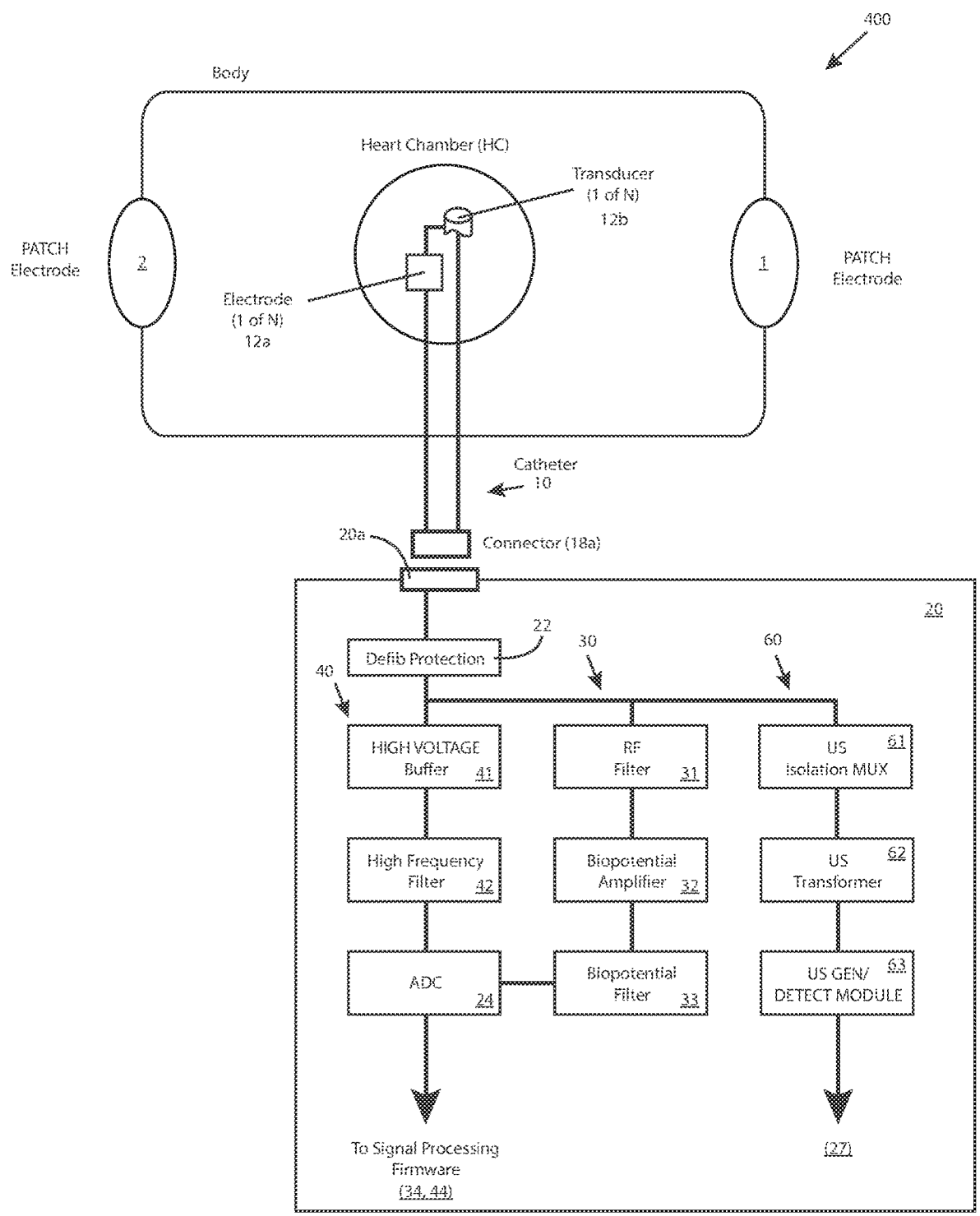
FIG. 4 provides a block diagram of another embodiment of a cardiac information processing system, in accordance with aspects of the inventive concept.

Referring now to FIG. 4, provided is a block diagram of an embodiment of a cardiac information processing system 400, in accordance with aspects of the inventive concept. The system 400 in FIG. 4 is similar to that of the system 100 in FIG. 1, except in FIG. 4 the catheter includes ultrasound transducers 12b, here located in the splines of the basket electrode array 12 with the electrodes 12a. In this embodiment, a single electrode 12a (e.g., for localization) is paired with an ultrasound transducer 12b (e.g., for anatomical representation). In one embodiment, there are 48 of such pairs on the electrode array 12. In other embodiments, the system can also localize electrodes not paired with transducers, such as with an AUX catheter and/or a catheter with only electrodes on an array. The catheter 10 also connects to cardiac information console 20 as described in FIG. 1.

With respect to the multiple "pairs" of electrical components, for example, at least one pair comprises an electrode 12a and an ultrasound transducer 12b. Each electrode 12a can be configured to record a voltage (or biopotential), such as the voltage present on a surface of the heart or at a location within a heart chamber HC. Each ultrasound transducer 12b can be configured to send and/or receive ultrasound signals, such as to produce an anatomical image of the tissue of at least a portion of the heart or other patient anatomical location. When such information is accumulated for multiple pairs 12a, 12b over time, an anatomical image of the heart with a superimposed mapping of cardiac activity can be produced for display via US subsystem 27.

In this embodiment, the cardiac information console 20 includes the same biopotential signal path 30 and localization signal path 40 described above with respect to FIG. 1, as well as DFIB protection module 22 and ADC 24. The BIO signal processing module 34 or the LOC signal processing module 44 are also included within cardiac information console 20, as well as UI subsystem 27. The power supply PWR and processor 26 can also be included, including BIO processor 36 and LOC processor 44.

Unlike FIG. 1, an ultrasound (US) signal path 60 is provided, which includes a US isolation MUX 61, US transformer 62, and US generation and detection module 63. The US isolation MUX 61 is connected to the DFIB protection module 22, and is used for turning on/off the US transducers 12b, such as in a predetermined order or pattern. The US isolation MUX 61 can be a set of high input impedance switches that, when open, isolate the US system and remaining US signal path elements, decoupling the impedance to ground (through the transducers and the US signal path 60) from the input of the LOC and BIO paths. The US isolation MUX 61 also multiplexes one transmit/receive circuit to one or more multiple transducers 12b on the catheter 10. The US transformer 62 operates in both directions between the US isolation MUX 61 and the US generation and detection module 63. US transformer 62 isolates the patient from the current generated by the US transmit and receive circuitry in module 63 during ultrasound transmission and receiving by the US transducers 12b. The switches of US transformer 62 selectively engage the transmit and/or receive electronics of module 63 based on the mode of operation of the transducers 12b, such as to activate one or more of the associated transducers 12b, such as in a predetermined order or pattern. That is, in a transmit mode, the module 63 receives a control signal from an US processor (within a data processor 26) that activates the US signal generation and connects an output of the transmit amplifier to US transformer 62. The US transformer 62 couples the signal to the US isolation MUX 61 which selectively activates the US transducers 12b. In a receive mode, the US isolation MUX 61 receives reflection signals from one or more of the transducers 12b, which are passed to the US transformer 62. The US transformer 62 couples signals into the receive electronics of the US generation and detection module 63, which in-turn transfers reflection data signals to the US processor for processing and use by the user interface system 27 and display 27a.

In this embodiment, the ADCs and the signal processing are all contained in the cardiac information console 20 for BIO, LOC, and ultrasound. Output to the ADC(s) is a sequence of individual biopotential voltage points for each electrode. As discussed below, these have been filtered and CMRR improved and normalized on a channel-by-channel basis with each channel handled independently. Output to the ADC is also a sequence of localization voltage points for each axis of each patch electrode. And output to the ADC 24 is also a collection of 48 (in this embodiment) reflection distances measured at a single time for ultrasound.

The algorithmic computations are done in the cardiac information console 20, including: process 48 or 80 channels at one time; measure propagation delays between signals; turn x, y, z data into a spatial distribution of location of electrodes; compute and apply corrections to the collection of positions; and/or turn individual distances into a point cloud and manipulate the point cloud.

Figure 5:
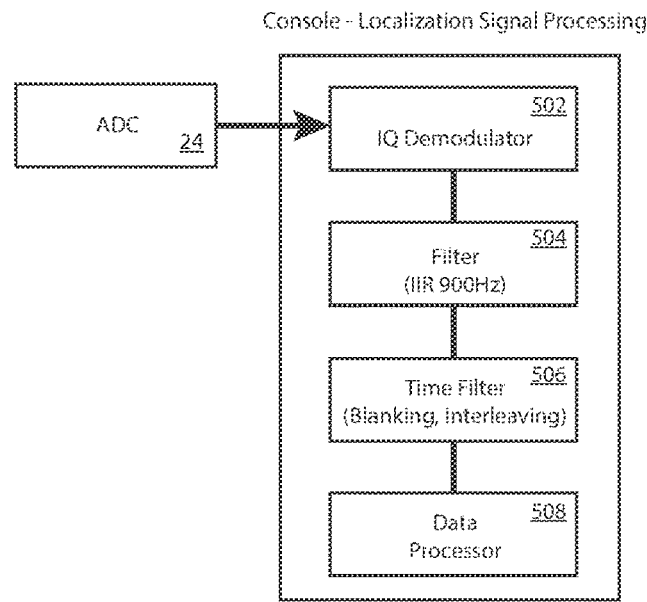
FIG. 5 provides a block diagram of an embodiment of functional elements that cooperate to perform localization signal processing, in accordance with aspects of the inventive concept.

FIG. 5 is a block diagram of an embodiment of functional elements that cooperate to perform localization signal processing, in accordance with aspects of the inventive concept. An IQ demodulator 502 receives outputs from an ADC 24, and analyzes the magnitude and phase of the received signal. In this embodiment, using IQ demodulation provides for maximum noise rejection. Narrowband filter 504 minimizes interference and a time filter 506 prevents intermodulation with ultrasound pulses by enabling selective filtering of signals from any time period. As examples, the time filter 506 can be used for blanking and interleaving signals, e.g., mapping signals, localization signals, and/or ultrasound imaging signals.

A data processor 508 can be configured to perform the computational algorithms applied to global data sets used in localization signal processing.

Figure 6:
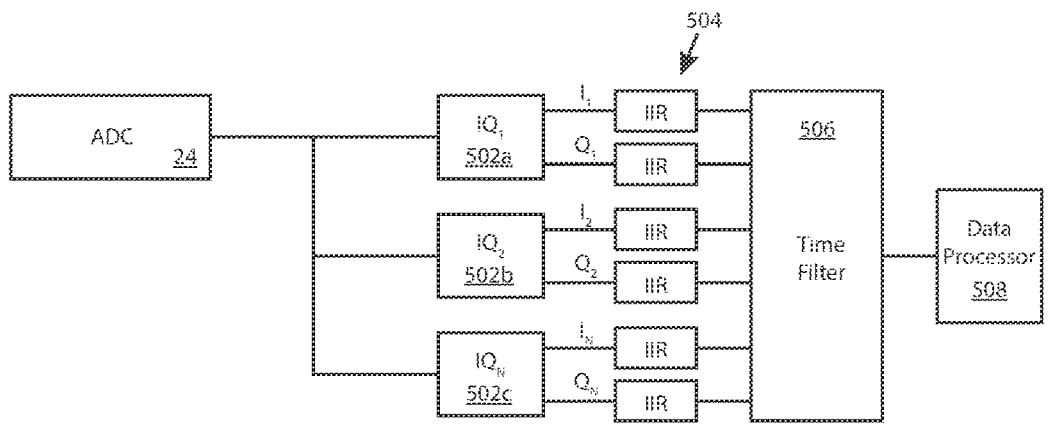
FIG. 6 is a block diagram of an embodiment of functional elements that cooperate to perform localization signal processing, as one implementation of the approach of FIG. 5, in accordance with aspects of the inventive concept.

FIG. 6 is a block diagram of an embodiment of functional elements that cooperate to perform localization signal processing, as another implementation of the approach of FIG. 5, in accordance with aspects of the inventive concept.

The embodiment of FIG. 6 shows simultaneous demodulation of multiple frequencies, in a parallel arrangement formed between the ADC 24 and the time filter 506. This embodiment produces highest throughput for localization and allows oversampling to reduce noise. There is an IQ demodulator 502a, 502b, 502c, for each channel coming from the ADC 24. As is shown, there is independent IIR filtering of I and Q components. This approach gives the highest possible signal integrity, with the narrowest band pass possible and the shortest real time delay. The time filter 506 prevents intermodulation with ultrasound pulses.

This approach provides a total synchronous processing chain and allows easy time/state dependent filters.

Figure 7:
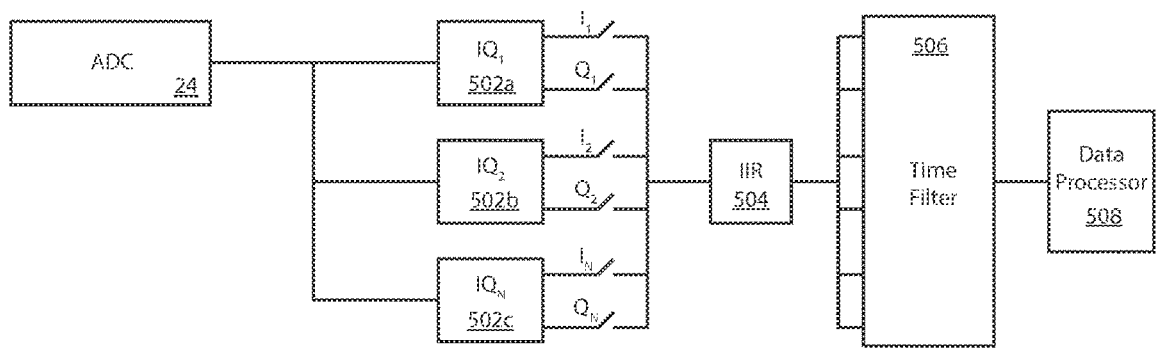
FIG. 7 is a block diagram of an embodiment of functional elements that cooperate to perform localization signal processing, as another implementation of the approach of FIG. 5, in accordance with aspects of the inventive concept.

FIG. 7 is a block diagram of an embodiment of functional elements that cooperate to perform localization signal processing, as another implementation of the approach of FIG. 5, in accordance with aspects of the inventive concept.

The embodiment of FIG. 7 is similar to that of FIG. 6, except there is not a dedicated IIR filter for each I and Q. Instead, there is a time multiplexing of IQ components, using switches, from the IQ demodulators into a multi-channel IIR filter 504. The multi-channel IIR filter 504 includes a sufficient number of channels to accommodate all Is and Qs. In other embodiments, the number of IIR filters 504 can be more than 1 and less than the number of Is and Qs.

This approach reduces computational resources with no additional time delay.

Figure 8:
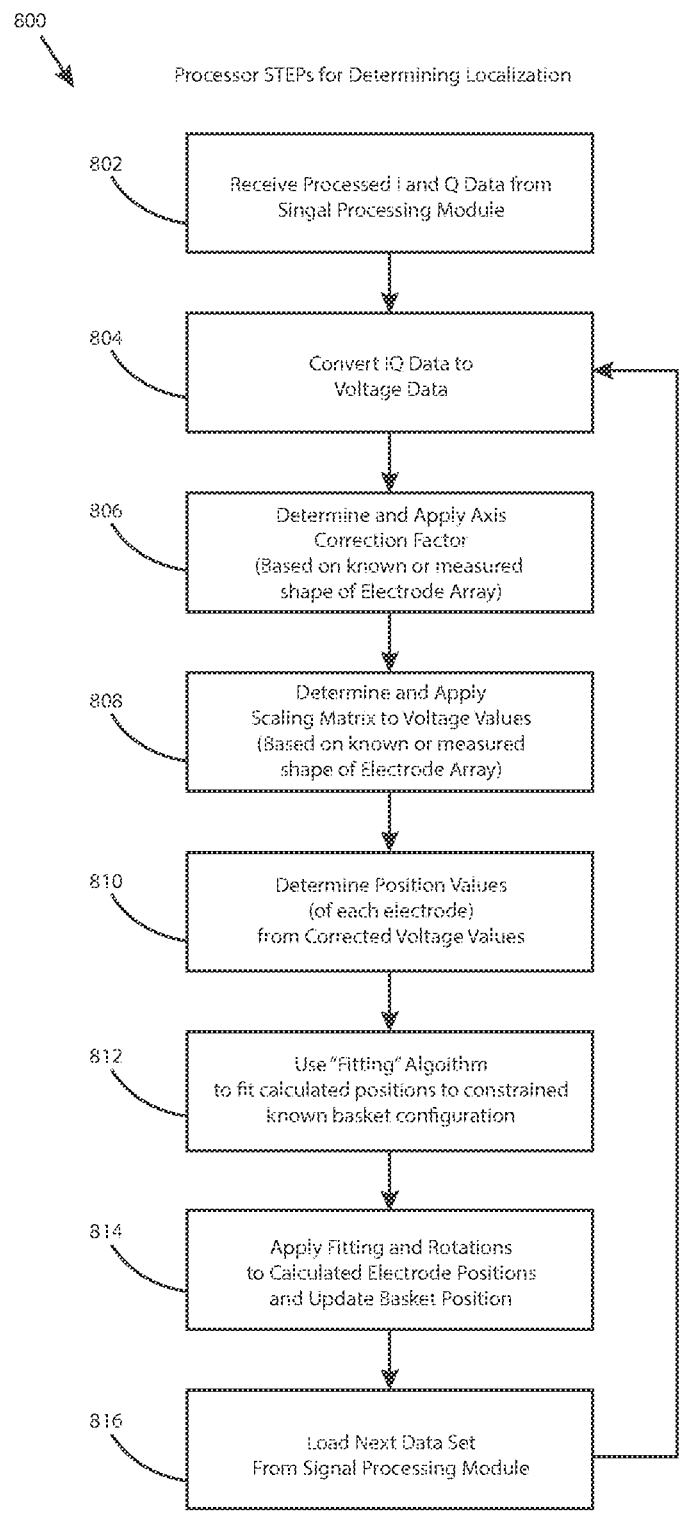
FIG. 8 is an embodiment of a localization method, in accordance with aspects of the inventive concepts.

FIG. 8 is an embodiment of a localization method, in accordance with aspects of the inventive concepts. The method 800 of FIG. 8 can be implemented by the various systems described herein.

In step 802, processed I and Q data is received from the signal processing module. In step 804, the IQ data is converted into voltage data. In some embodiments, the voltage data is filtered for abnormal signals and/or outlier data and this data can be excluded from further calculations. In step 806, an axis correction factor is determined and applied, which can be based on a known or measured shape of the electrode array, such as the 48 electrode array 12.

There is one axis for each pair of localization electrodes, e.g., reference electrodes 56. For instance, if the shape of the basket is incorrect, one or more axis can be rotated, scaled, and/or deskewed until the basket takes the proper shape, which could be visible on a display of the UI subsystem 27 and manipulatable user mechanisms of the user interface module 27. In step 808, a scaling matrix is determined and applied to the voltage values, again based on the known or measured shape of the electrode array. Here, if the length or size of the array is incorrect, based on the known or determined proportions of the electrode array, one or more of the axes can be scaled (longer or shorter) until the proper size is achieved.

In step 810, position values of the electrodes in the electrode array (e.g., electrode array 12) can be determined, and will have voltage values that are corrected based on steps 806 and 808. In step 812, a fitting algorithm can be performed to fit the calculated electrode positions to the known basket configuration. Additionally, in step 814, additional fitting and rotations can be applied to the calculated electrode positions and the electrode positions on the electrode array can be updated. This fitting step is more precise than the first fitting step, so provides better localization accuracy. In step 816, a next data set is loaded and the method returns to step 804 for further processing.

Figure 9:
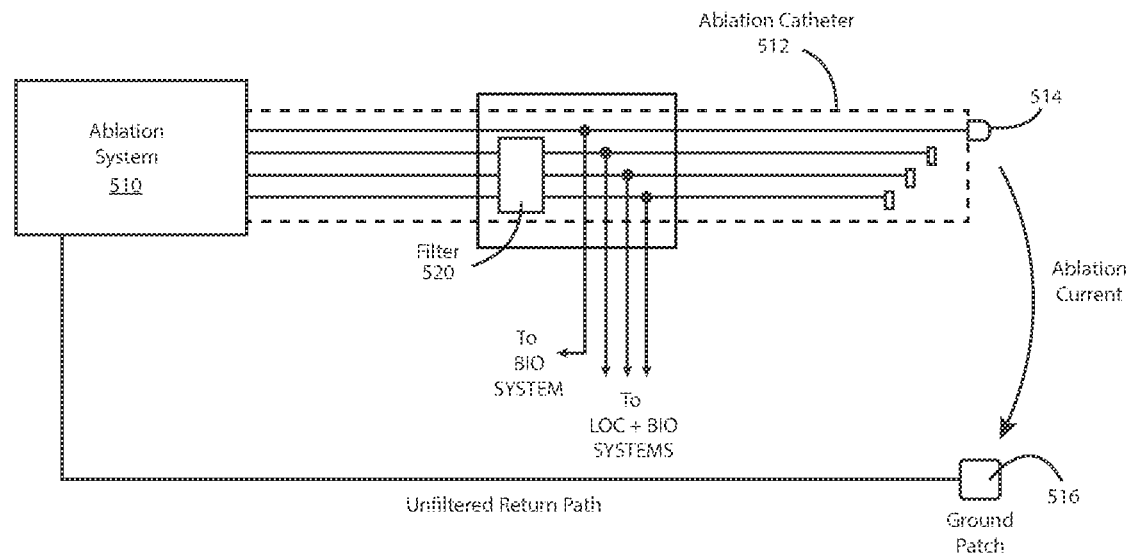
FIG. 9 is a schematic diagram of an ablation catheter, in accordance with aspects of the inventive concept.

FIG. 9 is a schematic diagram of an embodiment of an ablation system and an ablation catheter, in accordance with aspects of the inventive concept. There is an ablation system 510 coupled to an ablation catheter 512. An ablation tip 514 is located on a distal end of the ablation catheter 512. The ablation tip 514 delivers ablation energy to the tissue, e.g., RF ablation energy.

In this embodiment, there is no alteration to the "power path", e.g., no filtering of the power path, so no impedances are added to the chain and no ablation power is wasted in filters. There are filters 520 connected to non-ablation electrodes, e.g., electrodes used as part of a localization system. A high input impedance is maintained for the localization system, which allows localization during delivery of ablation energy. Additionally, in this embodiment, less ablation noise or artifact is coupled into the BIO and/or LOC signals than in the alternate configuration of a filter in the return path between the ablation system 510 and the ground patch 516.

Figure 10:
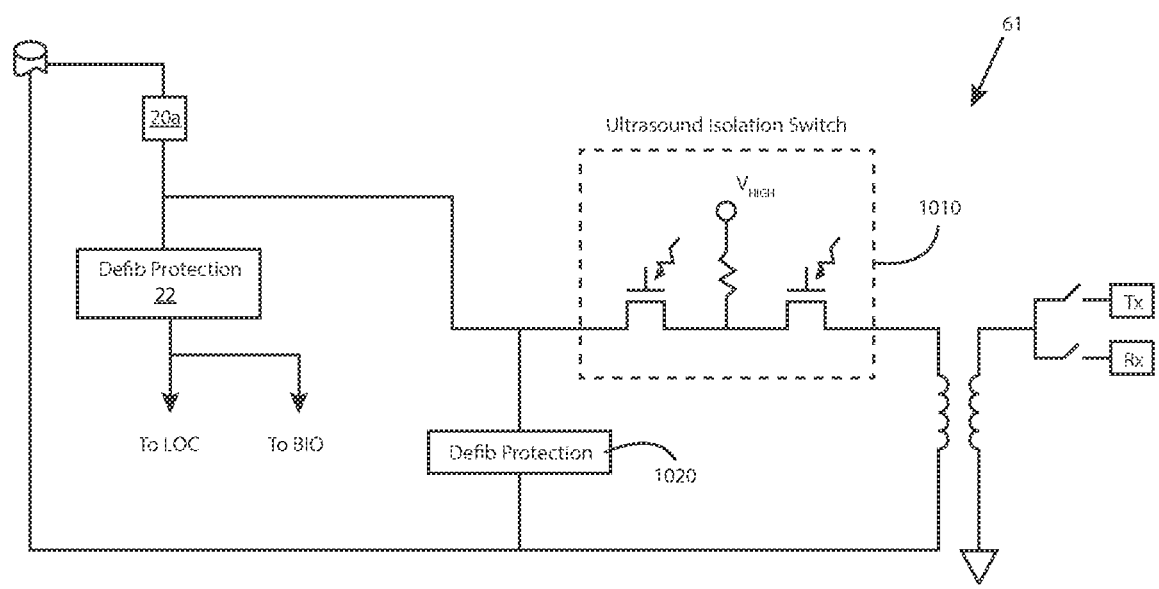
FIG. 10 is a schematic diagram of an ultrasound high input impedance switch, in accordance with aspects of the inventive concept.

FIG. 10 is a schematic diagram of an embodiment of ultrasound circuitry including an ultrasound high input impedance MUX 61, in accordance with aspects of the inventive concept. The ultrasound high input impedance switch includes ultrasound isolation switches 1010 (single switch shown). Ultrasound isolation switch 1010 connects in front of defibrillation (DFIB) protection module 22 discussed above, and has a separate DFIB protection circuit 1020 which connects to a port to which the localization, mapping, and auxiliary catheters (e.g., an ablation catheter) are connected (See, e.g., connector 20a FIG. 1).

This approach provides isolation of ultrasound from BIO and LOC signals. It is a minimum capacitance implementation, in which high voltage bias reduces capacitance and a symmetric switch minimizes charge injection. The high voltage also shortens the time for which the switch reaches an "on" state, and minimizes time of distortion for biopotential and localization signals. In one embodiment, OptoFETs isolate the control electronics from DFIB protection circuit 1020.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

We claim:

1. A localization system comprising:
   at least one catheter configured to deliver one or more catheter electrodes into a body cavity of a patient, the body cavity defined by surrounding tissue;
   a plurality of localization electrodes configured to be placed on the skin of the patient; and
   a cardiac information console configured to:
      provide localization drive signals to the plurality of localization electrodes to establish a coordinate system for the body cavity;
      determine both a magnitude and a phase of localization signals received from the one or more catheter electrodes; and
      process both the magnitude and the phase of the received localization signals to orient the catheter electrodes within the coordinate system.

2. The localization system according to claim 1, wherein the body cavity is a heart chamber and the surrounding tissue is one or more of the walls of the heart chamber.

3. The localization system according to claim 1, wherein the localization electrodes are configured to be placed in a fixed orientation on or relative to the skin of the patient.

4. The localization system according to claim 1, wherein the cardiac information console is further configured to record biopotential information from the one or more catheter electrodes.

5. The localization system according to claim 1, wherein the plurality of localization electrodes comprises a set of patch electrodes.

6. The localization system according to claim 5, wherein the plurality of localization electrodes includes one or more pairs of localization electrodes.

7. The localization system according to claim 6, wherein each pair of localization electrodes defines an axis of the coordinate system.

8. The localization system according to claim 7, wherein the one or more pairs of localization electrodes comprises three pairs of localization electrodes, and wherein each pair of localization electrodes defines one axis of the coordinate system.

9. The localization system according to claim 8, wherein the axes are non-orthogonal to a natural axis of the patient's body.

10. The localization system according to claim 1, further comprising a patient isolation drive system, wherein the cardiac information console provides the localization signals to the plurality of localization electrodes via the patient isolation drive system.

11. The localization system according to claim 1, wherein the catheter electrodes are disposed on a 3D array.

12. The localization system according to claim 11, wherein the 3D array includes a plurality of splines.

13. The localization system according to claim 11, wherein the 3D array comprises a basket array, a spiral array, a balloon array, an array with radially deployable arms, and/or other expandable and compactible structures.

14. The localization system according to claim 11, wherein the cardiac information console is further configured to generate an electronic representation of the 3D array of catheter electrodes from the recorded localization signals.

15. The localization system according to claim 14, wherein the cardiac information console is further configured to rotate the coordinate system to adjust and/or correct the electronic representation of the 3D array of catheter electrodes.

16. The localization system according to claim 15, wherein the cardiac information console is further configured to fit the electronic representation of the 3D array of catheter electrodes to a known or determined geometry of the 3D array of catheter electrodes.

17. The localization system according to claim 14, further comprising a user interface system configured to display the electronic representation of the 3D array of catheter electrodes.

18. The localization system according to claim 17, wherein the user interface system includes a mechanism that enables a user to rotate and/or scale the coordinate system to graphically adjust and/or correct an image of the electronic representation of the 3D array of catheter electrodes.

19. The localization system according to claim 1, wherein the at least one catheter further comprises one or more ultrasound transducers.

20. The localization system according to claim 19, wherein the cardiac information console is configured to collect image data using the one or more ultrasound transducers to generate one or more images of the body cavity surrounding tissue.

21. The localization system according to claim 1, wherein the cardiac information console further comprises for each catheter electrode:
- a biopotential signal path having a high impedance input and configured to receive biopotential signals from the catheter electrode; and
- a localization signal path having a high impedance input and configured to receive localization signals from the catheter electrode.

22. The localization system according to claim 21, wherein the cardiac information console further comprises a DFIB protection circuit coupled between the biopotential signal path and the localization signal path.

23. The localization system according to claim 21, wherein the cardiac information console further comprises for each catheter electrode:
- an ADC coupled to an output of the biopotential signal path and the localization signal path;
- an IQ demodulator coupled to an output of the ADC;
- a narrow band IIR filter coupled to the IQ demodulator; and
- a time filter coupled to the IIR filter and configured to selectively filter out portions of data on a time basis.

* * * * *